US007846690B2

(12) United States Patent
Grunwald

(10) Patent No.: US 7,846,690 B2
(45) Date of Patent: Dec. 7, 2010

(54) CLONING OF HONEY BEE ALLERGEN

(75) Inventor: Thomas Grunwald, Hamburg (DE)

(73) Assignee: PLS-Design GmbH, Hamburg (DE)

( * ) Notice: Subject to any disclaimer, the term of this patent is extended or adjusted under 35 U.S.C. 154(b) by 645 days.

(21) Appl. No.: 11/301,329

(22) Filed: Dec. 13, 2005

(65) Prior Publication Data

US 2006/0127394 A1 Jun. 15, 2006

Related U.S. Application Data

(60) Provisional application No. 60/635,479, filed on Dec. 14, 2004.

(51) Int. Cl.
*C12N 15/09* (2006.01)
*C12N 1/20* (2006.01)
*C12N 15/00* (2006.01)
*C12N 5/00* (2006.01)
*C12N 5/02* (2006.01)
*C07H 21/02* (2006.01)
*C07H 21/04* (2006.01)

(52) U.S. Cl. ................ 435/69.3; 435/252.3; 435/320.1; 435/325; 435/455; 536/23.1; 536/23.5

(58) Field of Classification Search ........................ None
See application file for complete search history.

(56) References Cited

U.S. PATENT DOCUMENTS 6,812,339 B1 * 11/2004 Venter et al. ............. 536/24.31
7,365,185 B2 * 4/2008 Boukharov et al. ........ 536/24.1
2004/0023291 A1 2/2004 Spertini

FOREIGN PATENT DOCUMENTS

GB 2 341 389 A 3/2000

OTHER PUBLICATIONS

Metzler et all Solution structure of human CTLA-4 and delineation of a CD80/CD86 binding site conserved in CD28.° Nature Structural Biol. 4:527-531, 1997.*
Bork et al. 'Powers and Pitfalls in Sequence Analysis: The 70% Hurdle.' Genome Research. 10:398-400, 2000.*
Doerks et al. 'Protein annotation: detective work for function prediction.' Trends in Genetics. 14:248-250, 1998.*
Smith et al. The challenges of genome sequence annotation or "the devil is in the details". Nat. Biotech.15:1222-1223, 1997.*
Brenner S. 'Errors in genome annotation.' Trends in Genetics 15:132-133, 1999.*
Bowie et al. Decipering the Message in Protein Sequences: Tolerance to Amino Acid Substitutions. Science 247:1306-1310, 1990.*
Lerner et al. 'Tapping the immunological repertoire to produce antibodies of predetermined specificity.' Nature. 299:593-596, 1982.*
Arbesman et al., "Allergenic potency of bee antigens measured by RAST inhibition", *Clinical Allergy*, vol. 6, pp. 587-594 (1976).
Barboni et al., "The Purification of Acid Phosphatase from Honey Bee Venom (*Apis Mellifica*)", *Toxicon*, vol. 25, No. 10, pp. 1097-1103 (1987).

Castro et al., "Biochemical properties and study of antigenic cross-reactivity between Africanized honey bee and wasp venom", *J. Invest. Allergol. Clin. Immunol.*, vol. 4(1), pp. 37-41 (1994).
Dotimas and Hider, "Honeybee Venom", *Bee World*, vol. 68(2), pp. 51-70 (1987).
Eich-Wanger and Müller, "Bee sting allergy in beekeepers", *Clinical and Experimental Allergy*, vol. 28, pp. 1292-1298 (1998).
Elbein, "The role of N-linked oligosaccharides in glycoprotein function", *TIBTECH*, vol. 9, pp. 346-352 (1991).
Gmachl and Kreil, "Bee venom hyaluronidase is homologous to a membrane protein of mammalian sperm", *Proc. Natl. Acad. Sci. USA*, vol. 90, pp. 3569-3573 (1993).
Grunwald et al., Database EMBL (Online), Accession No. DQ058012 (Jun. 5, 2005) (XP-002370247).
Grunwald et al., DATABASE UniProt (Online), Accession No. Q4TUB9 (Jul. 19, 2005) (XP-002370414).
Habermann, "Bienen- und Wespenstiche aus medizinischer Sicht", *Allgemeine Deutsche Imkerzeitung (ADIZ)*, vol. 11, p. 301-304 (1974).
Helbling et al., "Incidence of anaphylaxis with circulatory symptoms: a study over a 3-year period comprising 940 000 inhabitants of the Swiss Canton Bern", *Clin. Exp. Allergy*, vol. 34, pp. 285-290 (2004).
Hoffman et al., DATABASE UniProt (Online), Accession No. Q5BLY5 (Apr. 12, 2005) (XP-002370416).
Hoffman et al., DATABASE EMBL (Online), Accession No. AY939855 (Mar. 19, 2005) (XP 002370415).
Hoffman et al., "Allergens in *Hymenoptera* venom XXI. Cross-reactivity and multiple reactivity between fire ant venom and bee and wasp venoms", *J. Allergy Clin. Immunol.*, vol. 82, No. 5, Part 1, pp. 828-833 (1988).
Hoffman, "Hymenoptera Venom Proteins" in *Natural Toxins 2*, Eds. Singh and Tu, Plenum Press, New York and London (1996).
Hoffman and Shipman, "Allergens in bee venom", *J. Allergy Clin. Immunol.*, vol. 58, No. 5, pp. 551-562 (1976).
Hoffman et al., "Allergens in bee venom II. Two new high molecular weight allergenic specificities", *J. Allergy Clin. Immunol.*, vol. 59, No. 2, pp. 147-153 (1977).
Hunt et al., "A Controlled Trial of Immunotherapy in Insect Hypersensitivity", *The New England Journal of Medicine*, vol. 299, No. 4, pp. 157-161 (1978).
International Search Report from International Application No. PCT/EP2005/013397, issued Apr. 6, 2006.
Jacobsen and Hoffman, "Honey-bee venom acid phosphatase is a member of the prostatic acid phosphatase family", *J. Allergy Clin. Immunol.*, vol. 95, pp. 372 (1995).
Kettner et al., "Api m 6: A new bee venom allergen", *J. Allergy Clin. Immunol.*, vol. 107, No. 5, pp. 914-920 (2001).
Kettner et al., "IgE and T-cell responses to high-molecular weight allergens from bee venom", *Clinical and Experimental Allergy*, vol. 29, pp. 394-401 (1999).

(Continued)

Primary Examiner—Maher M. Haddad
Assistant Examiner—Nora M Rooney
(74) Attorney, Agent, or Firm—Arnold & Porter LLP

(57) ABSTRACT

The present invention relates to a nucleic acid encoding a polypeptide capable of binding to IgE from subjects allergic to venom of an insect from the order Hymenoptera having a homology of more than 70% to the amino acid sequence of SEQ ID NO: 2, which is the honey bee allergen Api m3 (acid phosphatase). The invention further relates to expression vectors, host cells and polypeptides encoded by the nucleic acid, as well as diagnostic and pharmaceutical uses thereof.

23 Claims, 8 Drawing Sheets

OTHER PUBLICATIONS

Kuchler et al., "Analysis of the cDNA for phospholipase $A_2$ from honeybee venom glands The deduced amino acid sequence reveals homology to the corresponding vertebrate enzymes", *Eur. J. Biochem*, vol. 184, pp. 249-254 (1989).

Kulike, "Zur Struktur und Funktion des Hymenopterenstachels", Amts- und Mitteilungsblatt der Bundesanstalt für Materialprüfung, vol. 16, pp. 519-550 (1986).

Müller, "New Developments in the Diagnosis and Treatment of Hymenoptera Venom Allergy", *Int. Arch. Allergy Immunol.*, vol. 124, pp. 447-453 (2001).

Müller, "Recombinant Hymenoptera venom allergens", *Allergy*, vol. 57, pp. 570-576 (2002).

Schiavino et al., "Specific ultrarush desensitization in Hymenoptera venom-allergic patients", *Anals of Allergy, Asthma, & Immunology*, vol. 92, pp. 409-413 (2004).

Sobotka et al., "Honeybee venom: Phospholipase A as the major allergen", *J. Clin. Allergy Clin. Immunol.*, vol. 53, p. 103, Abstract No. 96, (1974).

Sobotka et al., "Allergy to insect stings II. Phospholipase A: The major allergen in honeybee venom", *J. Allergy Clin. Immunol.*, vol. 57, No. 1, pp. 29-40 (1976).

Soldatova et al., DATABASE EMBL (Online), Accession No. AF205594 (Nov. 8, 2005) (XP-002370417).

Soldatova et al., DATABASE UniProt (Online), Accession No. Q336K2, (Dec. 6, 2005) (XP-002370418).

Soldatova, "Biological Activity of Recombinant Bee Venom Allergens Expressed in Baculovirus-infected Cells", *Arbeiten Aus Dem Paul-Ehrlich-Institut*, 9th International Paul-Ehrlich-Seminar, No. 9, pp. 189-193 (1999).

Soldatova et al., "Superior biologic activity of the recombinant bee venom allergen hyaluronidase expressed in baculovirus-infected insect cells as compared with *Escherichia coli*", *J. Allergy Clin. Immunol.*, vol. 101, No. 5, pp. 691-698 (1998).

Soldatova et al., "Molecular Cloning of a New Honeybee Venom Allergen, Acid Phosphatase", *J. Allergy Clin. Immunol.*, Abstracts, p. S378, Abstract No. 1105 (2000).

Sudowe et al., "Efficacy of recombinant adenovirus as vector for allergen gene therapy in a mouse model of type I allergy", *Gene Therapy*, vol. 9, pp. 147-156 (2002).

Vlasak et al., "Nucleotide sequence of cloned cDNA coding for honeybee prepromelittin", *Eur. J. Biochem.*, vol. 135, pp. 123-126 (1983).

Wypych et al., "Analysis of Differing Patterns of Cross-Reactivity of Honeybee and Yellow Jacket Venom-Specific IgE: Use of Purified Venom Fractions", *Int. Arch. Allergy. Appl. Immunol.*, vol. 89, pp. 60-66 (1989).

* cited by examiner

Fig. 1

```
LOCUS       Api m 3    1122 bp    DNA
SOURCE      Tissue, venom gland
ORGANISM    Apis mellifera
BASE COUNT     362 a     214 c     238 g     308 t
ORIGIN
    1 gaacttaaac aaataaatgt gatattccgg cacggcgata ggatacccga tgagaaaaac
   61 gaaatgtatc cgaaagatcc ttatttgtat tatgattttt atccactgga gcgtggcgaa
  121 ttgactaact caggtaaaat gcgagaatat caattggggc aattcttgag agagagatat
  181 ggtgactttt tgggagacat ttacacggaa gaatccgtct cggctctcag ctcgttctac
  241 gataggacga aaatgtctct gcaactcgta ctcgcggcgc tctatccgcc aaataaattg
  301 caacaatgga acgaagatct gaactggcaa ccgatcgcca cgaaatattt gcgccgctac
  361 gaggacaata tcttttttgcc agaagattgt ttgttattta ccatcgaact tgatagagta
  421 ttggaatcac cgcgtggaaa gtatgaattc tcgaaatatg acaaattgaa gaaaaaattg
  481 gaagaatgga ccggaaaaaa tatcactacg ccatgggatt attattacat atatcataca
  541 ctggtggctg aacaatcgta cggtcttact ctgccatctt ggacaaataa tatattcccg
  601 agaggagaat tgttcgatgc gacggtattt acgtacaaca taaccaattc gactcctttg
  661 ttgaaaaaac tttatggagg tccgcttctt cgaatattca ccaagcatat gttagacgtg
  721 gtatcgggta cgcaaaagaa aaagcgaaag atatacttgt tcagtggaca tgaaagtaat
  781 atcgcctctg tgttgcacgc tcttcaactt tattatcctc acgttcctga atattccagt
  841 tctattataa tggagcttca caatatcgaa ggcactcact acgtaaagat cgttactac
  901 ttgggtatcc cgtctgaagc gagagaactt caattacccg gctgcgaggt actttgccct
  961 ttgtacaaat atttacaatt gatagagaac gtgataccat cgaacgaaga gttgatctgc
 1021 gataaaagat tcgtcgacga atcggcaaac aatttgtcga tcgaagaatt agatttcgtg
 1081 aaattgaacc taataaggat agcgggtact gagaataagt aa
//
```

Fig 2:

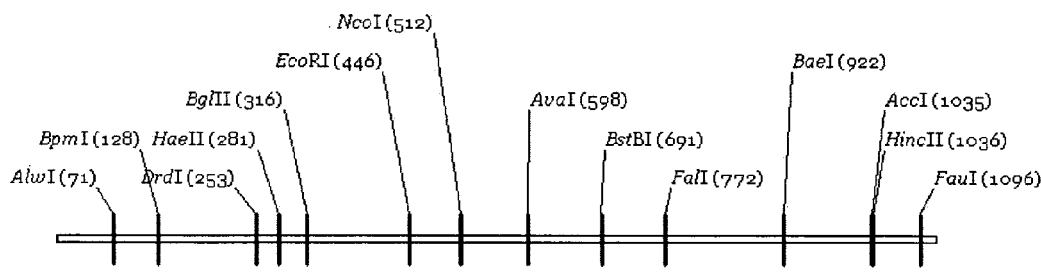

Api m 3

```
LOCUS        Translatio      374 aa
DEFINITION   Translation of cloned Api m 3
KEYWORDS     TRANSLATED.
SOURCE       Tissue, venom gland
ORIGIN
     1  ELKQINVIFR  HGDRIPDEKN  EMYPKDPYLY  YDFYPLERGE  LTNSGKMREY  QLGQFLRERY
    61  GDFLGDIYTE  ESVSALSSFY  DRTKMSLQLV  LAALYPPNKL  QQWNEDLNWQ  PIATKYLRRY
   121  EDNIFLPEDC  LLFTIELDRV  LESPRGKYEF  SKYDKLKKKL  EEWTGKNITT  PWDYYYIYHT
   181  LVAEQSYGLT  LPSWTNNIFP  RGELFDATVF  TYNITNSTPL  LKKLYGGPLL  RIFTKHMLDV
   241  VSGTQKKKRK  IYLFSGHESN  IASVLHALQL  YYPHVPEYSS  SIIMELHNIE  GTHYVKIVYY
   301  LGIPSEAREL  QLPGCEVLCP  LYKYLQLIEN  VIPSNEELIC  DKRFVDESAN  NLSIEELDFV
   361  KLNLIRIAGT  ENK*
```

Fig. 4A

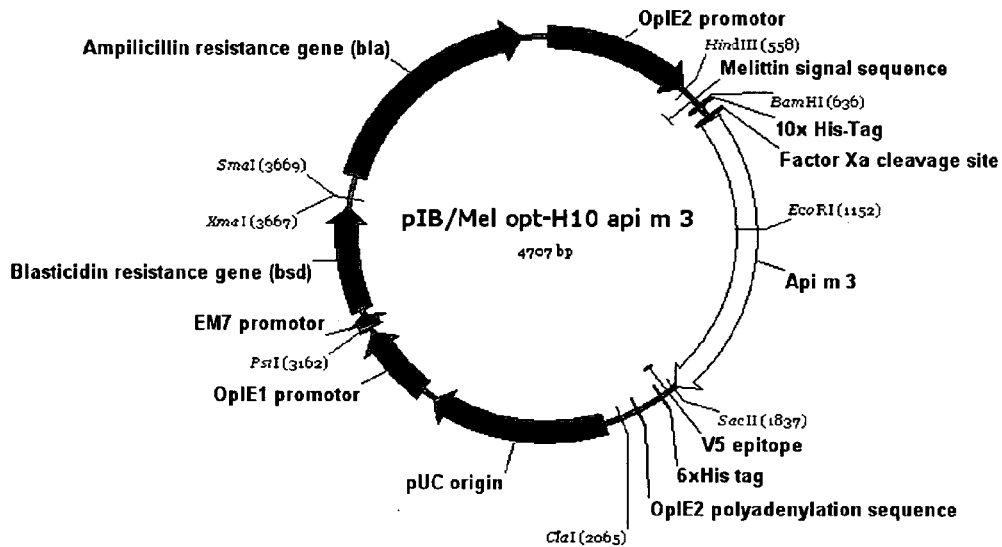

Fig. 4B a) AAGCTTATGAAATTC
          M   K  F b) AAGCTTTCC<u>GCCATGG</u>CGAAATTC
               M  A  K  F

Fig. 5A

| Order of alignment positions (Hoffman) | Order of alignment positions (this invention) | Sequences of published peptide fragments | AA length |
|---|---|---|---|
| 1 | 1,4 | ELKQINVIFRHGDRIPDEKNEMYPKKLEEWTDK | 33 |
| 2 | 8 | FVDESANNLSIEEIDFVK | 18 |
| 3 | 2 | LQQWNEDLNWQPIATK | 16 |
| 4 | 3 | GKYEFSKR | 8 |
| 5 | - | YNIFAGTWK | 9 |
| 6 | 6 | LYGGPLLRDNYVGDER | 16 |
| 7 | 5,7 | DITTPKDYYYIYHTLVAENEYSSCIIMEYHNIEGTHYVKIVYYLGIPSEARELQLPGCEVLCPLEKYLQLIENVIPSNEELICDKR | 86 |

Fig. 5B

```
                *         20            *         40            *
Api m 3 :   ELKQINVIFRHGDRIPDEKNEMYPKDPYLYYDFYPLERGELTNSGKMREY  :  50
Hoffman :   ELKQINVIFRHGDRIPDEKNEMYPKKL-EEWTDK
Revised :   ELKQINVIFRHGDRIPDEKNEMYPK 60            *         80            *        100
Api m 3 :   QLGQFLRERYGDFLGDIYTEESVSALSSFYDRTKMSLQLVLAALYPPNKL :  100
Hoffman :                   FVDESANNLSIEEIDFVK                        L
Revised :                                                            L

*        120            *        140            *
Api m 3 :   QQWNEDLNWQPIATKYLRRYEDNIFLPEDCLLFTIELDRVLESPRGKYEF :  150
Hoffman :   QQWNEDLNWQPIATK                                    GKYEFSKR
Revised :   QQWNEDLNWQPIATK                                    GKYEF 160            *        180            *        200
Api m 3 :   SKYDKLKKKLEEWTGKNITTPWDYYYIYHTLVAEQSYGLTLPSWTNNIFP :  200
Hoffman :                  YNIFAGTWK
Revised :   SK      KLEEWT     ITTPKDYYYIYHTLVAE

*        220            *        240            *
Api m 3 :   RGELFDATVFTYNITNSTPLLKKLYGGPLLRIFTKHMLDVVSGTQKKKRK :  250
Hoffman :                              LYGGPLLRDNYVGDER
Revised :                              LYGGPLLR 260            *        280            *        300
Api m 3 :   IYLFSGHESNIASVLHALQLYYPHVPEYSSSIIMELHNIEGTHYVKIVYY :  300
Hoffman :            DITTPKDYYYIYHTLVAENEYSSCIIMEYHNIEGTHYVKIVYY
Revised :                                 EYSSCIIMEYHNIEGTHYVKIVYY

*        320            *        340            *
Api m 3 :   LGIPSEARELQLPGCEVLCPLYKYLQLIENVIPSNEELICDKRFVDESAN :  350
Hoffman :   LGIPSEARELQLPGCEVLCPLEKYLQLIENVIPSNEELICDKR
Revised :   LGIPSEARELQLPGCEVLCPLEKYLQLIENVIPSNEELICDKRFVDESAN 360                *
Api m 3 :   NLSIEELDFVKLNLIRIAGTENK- :  373
Hoffman :
Revised :   NLSIEEIDFVK
```

Fig 7

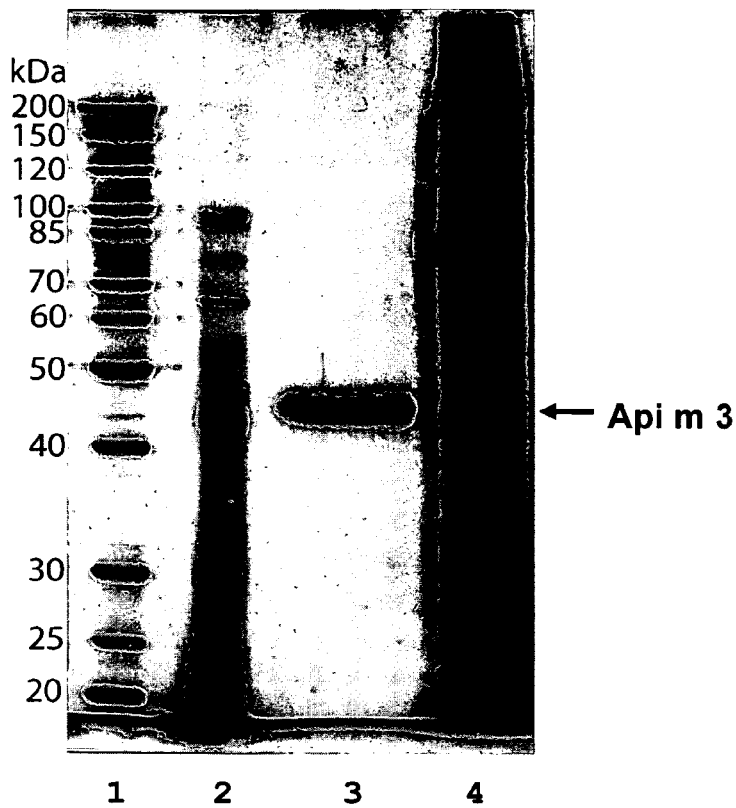

Fig 8

```
                            RHGXRXP motif
Api m 3    (A. mellif.)  ELKQINVIFRHGDRXPDEKNEMYPKDPYLYYDFYPLERGELTNSGKMREYQLGQFLRERYGDFLGDIYTEESVSALSSFY  80
Acph 1     (D. melanog.) QLKFVEVIYRHGDRTP---VDPYPTDPWGDRKFWPTGWGDLTNLGRQEHYDLGKWLRNRYSNLLPPIYSNENIYVQSTDV  77
CG7899-PA  (D. melanog.) QLKFVEVIYRHGDRTP---VDPYPTDPWGDRKFWPTGWGDLTNLGRQEHYDLGKWLRNRYSNLLPPIYSNENIYVQSTDV  77
Acph 1     (D. suboscura.) ELKFAEVIFRHGDRTP---VDPYPTDPWNNRKFWPTGWGQLTNLGKEQHYELGKWLRNRYKSLLGSRYTNEDIFVQSTDV  77
CG9451-PA  (D. melanog.) TLKLVEVLFRHGERTP---VSTYFNDPYINETYEPFGWGALTNGAKVELYKIGKQLRQRYKDFLPAYYQPDAIRAQSSES  77
                          **  :*::*** *  *    . **.**:    :       * *** .*  *.  *: **. **  .:  :  . *:

Api m 3    (A. mellif.)  DRTKMSLQLVLAALYPP-NKLQQWNEDLNWQPIATKYLRR-YEDNIFLPEDCLLFTIELDRVLESPRGKYEFSRYDKLRK  159
Acph 1     (D. melanog.) DRTLMSAQSNLAGLYEP-QGEDIWNTDINWQPIPIHTSPEREDPILAAKAPCPAYDYELASLESSPEFKALTEKHRNLFA  156
CG7899-PA  (D. melanog.) DRTLMSAQSNLAGLYEP-QGEDIWNTDINWQPIPIHTSPEREDPILAAKAPCPAYDYELASLESSPEFKALTEKHRNLFA  156
Acph 1     (D. suboscura.) DRTLMSAQSDLAGLYEP-QGDDIWNPRIDWQPVPVHTVPEKDDSILAARASCPAYDYELATLEASSEFQALYVRYRELLS  156
CG9451-PA  (D. melanog.) PRTLMSMQMVLAGLFPPENTPMEWNQLLNWQPIPIVMEPEETDVHIRMKAPCPRYDESVLEVIELPEVVKKLHAESSDLLR  157
                          ** **  ** *.*: *      **  ::*:::           :    :     * :  .:   ::        : .*

Api m 3    (A. mellif.)  KLEEWTGKNLSTPWDYYYIYHTLVAEQSYGLTLPSWTNNIFPRGELFDATVPTYNLTNSIPLLKKLYGGPLLRIFTKHML  238
Acph 1     (D. melanog.) YLSEKGGRPVRTFIDAQYLNNTLFIENLYNMTLPKWTKKVYGREELTYVSNPAFAISSYTRKLARLKAGPLLKDIFQRFK  236
CG7899-PA  (D. melanog.) YLSEKGGRPVRTFIDAQYLNNTLFIENLYNMTLPKWTRMVYGREELTYVSNPAFAISSYTRKLARLKAGPLLKDIFQRFK  236
Acph 1     (D. suboscura.) YLTQNSGRHVKSFIDAQYLNNTLFIERLYNMTLPVWAEKVYGKEELTYVSNPAFSIATFTRSMARLKTGPLLKDIFERFD  236
CG9451-PA  (D. melanog.) ELTTHTGLNITHAHDVTNVFITLLCEQTFGLQLPSWTNDYFP-ERMLPLAEKSYVYDAYTTEQRRMKGGFFVELLLKQMQ  236
                          *    *    .:   *   *    *  **.  :: .:  **  *::  :  ::  *      ::  *  ::. : ::

Api m 3    (A. mellif.)  DVVSGTQK-KRRKIYLFSGHESNIASVLHALQLYYPHVPEYSSSIIMELHN--IEGTHYVKIVYYLGIPSEARELQLPGC  315
Acph 1     (D. melanog.) EKSSGSLR-PDRSMWVYSAHDTTVASVLNALKLFELHSPPYTACIMMELRVD--ETNTPLVSIFYKNTTAEPLPLDIPGC  313
CG7899-PA  (D. melanog.) EKSSGSLR-PDRSMWVYSAHDTTVASVLNALKLFELHSPPYTACIMMELRVD--ETNTPLVSIFYKNTTAEPLPLDIPGC  313
Acph 1     (D. suboscura.) KKLNNQLK-PDRSLWIYSAHDTTIANVLNSLKLFELHSPPYAACIMLEMRVD--DSNTPLVSVFYKNTTAEPLPLDIPGC  313
CG9451-PA  (D. melanog.) DRISGALKPANRRMFLSCGHDWTITNVLSALNVWEAQMPRFSSLIAFELHQNPQTGEYFLEIYFQNDPHKEPQQLQIPGC  316
                          :  .  *   .*..:: . *:   *::. * :   *      :*.** *.   :        *   :   *  *:**

Api m 3    (A. mellif.)  EVLCPLYKYLQLIENVIPSNEELICDKRFVDESANNLSIEELDFVKLNLIRIAGTENK---------------------  373
Acph 1     (D. melanog.) GPSCPLTRLMNIYEDVLPVDWERECKLSTMMMTYEEANLGTATGILILIVIALLFASYGLMIYRRRNYKLYSSYSQMA  392
CG7899-PA  (D. melanog.) GPSCPLTRLMNIYEDVLPVDWERECKLSTMMMTYEEANLGTATGILILIVIALLFASYGLMIYRRRNYKLYSSYSQMA  392
Acph 1     (D. suboscura.) GLSCPLKRTLVKLYQDVLPGNWERECKRSTMMMTYEEANLGAATGILIFIITVLLCASYGLMVYRRRHYNLYTSYSQMA  392
CG9451-PA  (D. melanog.) EKQCPIGKLLELTKDIIPDAPYAELCKAKGTQGGAKISYH-------------------------------------  356
                          ** :  .  ::: ::::: *      . :                :  .
```

Fig 9
| residues | mass calculated | measured | sequence |
|---|---|---|---|
| 28 - 34 | 889.52 | 889.55 | QINVIFR |
| 50 - 62 | 1753.81 | 1753.85 | DPYLYYDFYPLER |
| 73 - 81 | 1153.60 | 1153.64 | EYQLGQFLR |
| 248 - 255 | 888.53 | 888.54 | LYGGPLLR |
| 260 - 270 | 1214.62 | 1214.65 | HMLDVVSGTQK |
| 321 - 332 | 1380.75 | 1380.82 | IVYYLGIPSEAR |
Fig 10
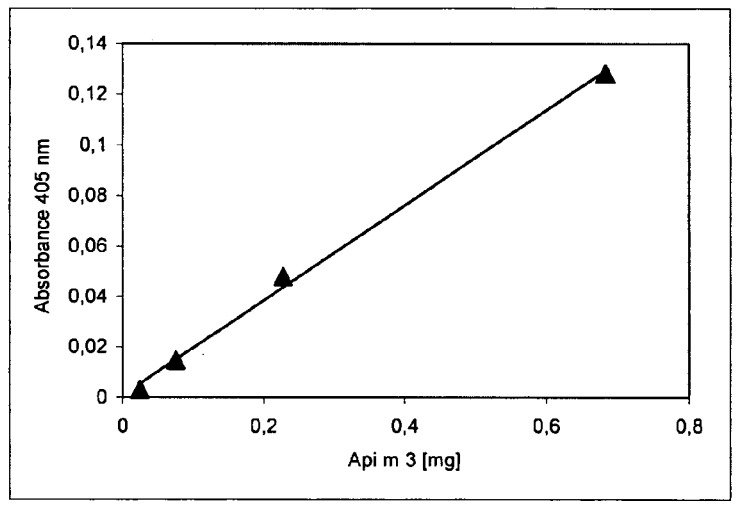
Fig 11
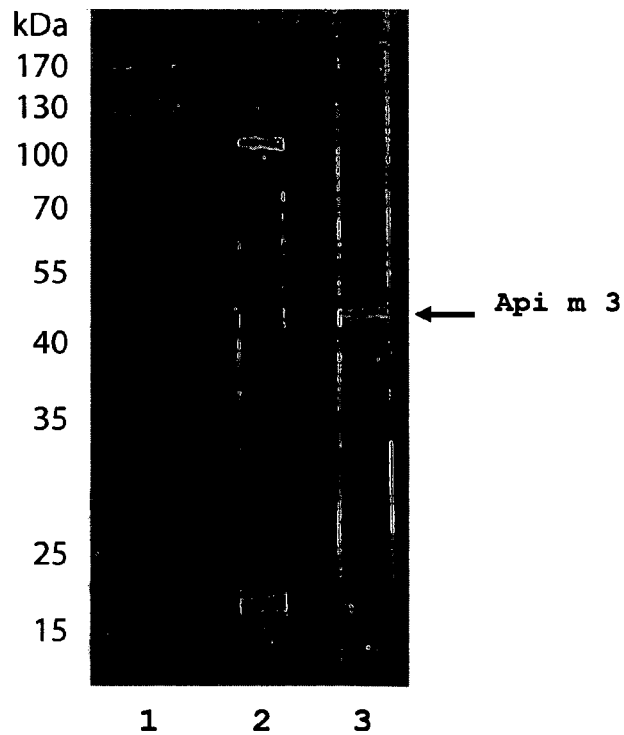

Fig 12
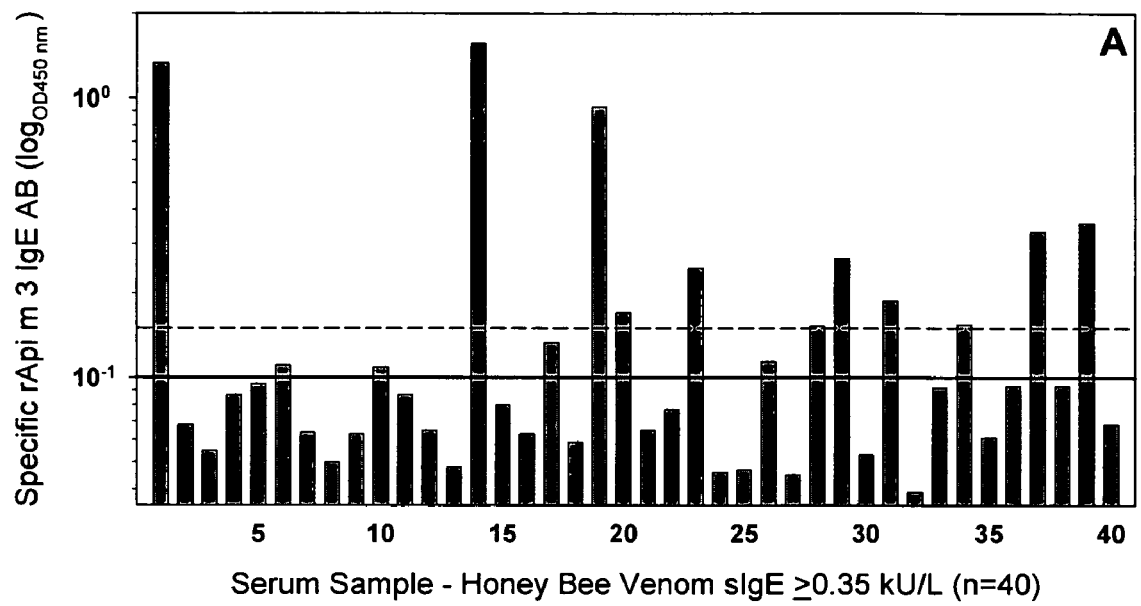
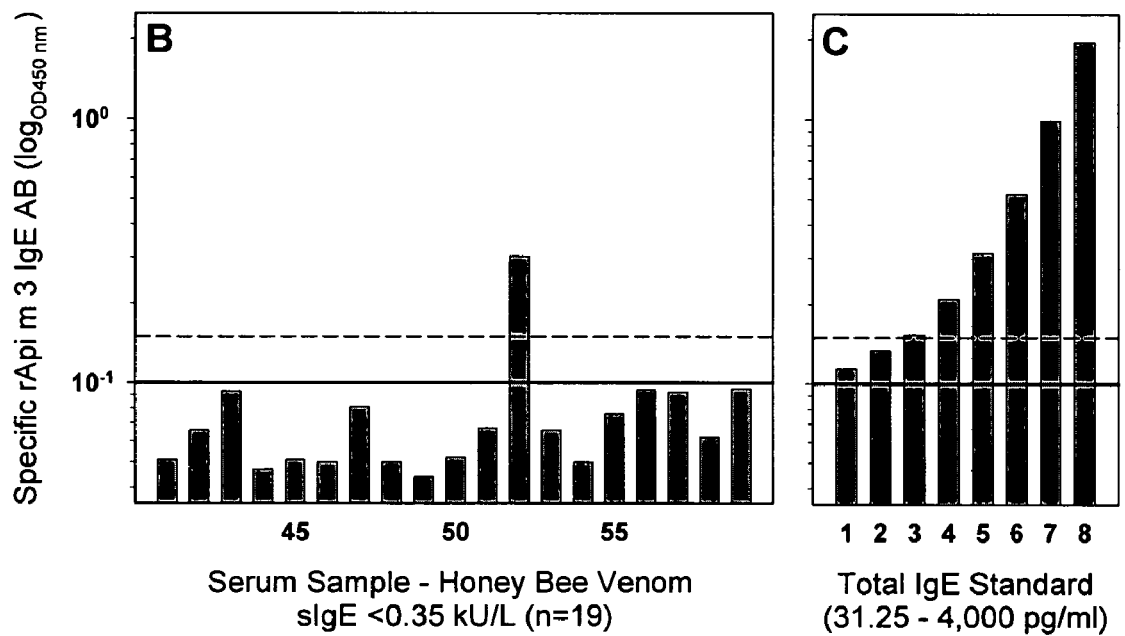

SEQUENCE LISTING

<160> NUMBER OF SEQ ID NOS: 41

<210> SEQ ID NO 1
<211> LENGTH: 1122
<212> TYPE: DNA
<213> ORGANISM: Apis mellifera

<400> SEQUENCE: 1

```
gaacttaaac aaataaatgt gatattccgg cacggcgata ggatacccga tgagaaaaac      60
gaaatgtatc cgaaagatcc ttatttgtat tatgattttt atccactgga gcgtggcgaa     120
ttgactaact caggtaaaat gcgagaatat caattggggc aattcttgag agagagatat     180
ggtgactttt tgggagacat ttacacggaa gaatccgtct cggctctcag ctcgttctac     240
gataggacga aaatgtctct gcaactcgta ctcgcggcgc tctatccgcc aaataaattg     300
caacaatgga acgaagatct gaactggcaa ccgatcgcca cgaaatattt gcgccgctac     360
gaggacaata tcttttttgcc agaagattgt ttgttattta ccatcgaact tgatagagta     420
ttggaatcac cgcgtggaaa gtatgaattc tcgaaatatg acaaattgaa gaaaaaattg     480
gaagaatgga ccggaaaaaa tatcactacg ccatgggatt attattacat atatcataca     540
ctggtggctg aacaatcgta cggtcttact ctgccatctg acaaataat atattcccga     600 gaggagaatt gttcgatgcg acggtattta cgtacaacat aaccaattcg actcctttgt     660
tgaaaaaact ttatggaggt ccgcttcttc gaatattcac caagcatatg ttagacgtgg     720
tatcgggtac gcaaaagaaa aagcgaaaga tatacttgtt cagtggacat gaaagtaata     780
tcgcctctgt gttgcacgct cttcaacttt attatcctca cgttcctgaa tattccagtt     840
ctattataat ggagcttcac aatatcgaag gcactcacta cgtaaagatc gtttactact     900
tgggtatccc gtctgaagcg agagaacttc aattacccgg ctgcgaggta ctttgccctt     960
tgtacaaata tttacaattg atagagaacg tgataccatc gaacgaagag ttgatctgcg    1020
ataaaagatt cgtcgacgaa tcggcaaaca atttgtcgat cgaagaatta gatttcgtga    1080
aattgaacct aataaggata gcgggtactg agaataagta aa                       1122
```

<210> SEQ ID NO 2
<211> LENGTH: 373
<212> TYPE: PRT
<213> ORGANISM: Apis mellifera

<400> SEQUENCE: 2

```
Glu Leu Lys Gln Ile Asn Val Ile Phe Arg His Gly Asp Arg Ile Pro
1               5                   10                  15

Asp Glu Lys Asn Glu Met Tyr Pro Lys Asp Pro Tyr Leu Tyr Tyr Asp
            20                  25                  30
```

-continued

```
Phe Tyr Pro Leu Glu Arg Gly Glu Leu Thr Asn Ser Gly Lys Met Arg
         35                  40                  45

Glu Tyr Gln Leu Gly Gln Phe Leu Arg Glu Arg Tyr Gly Asp Phe Leu
 50                  55                  60

Gly Asp Ile Tyr Thr Glu Ser Val Ser Ala Leu Ser Ser Phe Tyr
 65                  70                  75                  80

Asp Arg Thr Lys Met Ser Leu Gln Leu Val Leu Ala Ala Leu Tyr Pro
                 85                  90                  95

Pro Asn Lys Leu Gln Gln Trp Asn Glu Asp Leu Asn Trp Gln Pro Ile
                100                 105                 110

Ala Thr Lys Tyr Leu Arg Arg Tyr Glu Asp Asn Ile Phe Leu Pro Glu
             115                 120                 125

Asp Cys Leu Leu Phe Thr Ile Glu Leu Asp Arg Val Leu Glu Ser Pro
         130                 135                 140

Arg Gly Lys Tyr Glu Phe Ser Lys Tyr Asp Lys Leu Lys Lys Lys Leu
145                 150                 155                 160

Glu Glu Trp Thr Gly Lys Asn Ile Thr Thr Pro Trp Asp Tyr Tyr
                165                 170                 175

Ile Tyr His Thr Leu Val Ala Glu Gln Ser Tyr Gly Leu Thr Leu Pro
                180                 185                 190

Ser Trp Thr Asn Asn Ile Phe Pro Arg Gly Glu Leu Phe Asp Ala Thr
            195                 200                 205

Val Phe Thr Tyr Asn Ile Thr Asn Ser Thr Pro Leu Leu Lys Lys Leu
        210                 215                 220

Tyr Gly Gly Pro Leu Leu Arg Ile Phe Thr Lys His Met Leu Asp Val
225                 230                 235                 240

Val Ser Gly Thr Gln Lys Lys Arg Lys Ile Tyr Leu Phe Ser Gly
                245                 250                 255

His Glu Ser Asn Ile Ala Ser Val Leu His Ala Leu Gln Leu Tyr Tyr
            260                 265                 270

Pro His Val Pro Glu Tyr Ser Ser Ile Ile Met Glu Leu His Asn
        275                 280                 285

Ile Glu Gly Thr His Tyr Val Lys Ile Val Tyr Leu Gly Ile Pro
    290                 295                 300

Ser Glu Ala Arg Glu Leu Gln Leu Pro Gly Cys Glu Val Leu Cys Pro
305                 310                 315                 320

Leu Tyr Lys Tyr Leu Gln Leu Ile Glu Asn Val Ile Pro Ser Asn Glu
                325                 330                 335

Glu Leu Ile Cys Asp Lys Arg Phe Val Asp Glu Ser Ala Asn Asn Leu
            340                 345                 350

Ser Ile Glu Glu Leu Asp Phe Val Lys Leu Asn Leu Ile Arg Ile Ala
        355                 360                 365

Gly Thr Glu Asn Lys
        370

<210> SEQ ID NO 3
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
gaacttaaac aaataaatgt g                                              21
```

<210> SEQ ID NO 4
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
aaccgcggtt acttacttat tctcagtacc cg                                    32

<210> SEQ ID NO 5
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
gtaaaacgac ggccagtgcc aa                                               22

<210> SEQ ID NO 6
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
caggaaacag ctatgaccat ga                                               22

<210> SEQ ID NO 7
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
ggaaagcttt ccgccatggc gaaattctta gtc                                   33

<210> SEQ ID NO 8
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
cgggatcccg catagatgta agaaatg                                          27

<210> SEQ ID NO 9
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
ctgaatagcg ccggatccga ccat                                             24

```
<210> SEQ ID NO 10
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
ccctctagac tcgagccaat gatg                                          24

<210> SEQ ID NO 11
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
gggatatccc ttccctcgat ccctctagac tc                                 32

<210> SEQ ID NO 12
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
agaatttcat atgaaattct tagtcaacg                                     29

<210> SEQ ID NO 13
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
aagagctctt acttacttat tctcag                                        26

<210> SEQ ID NO 14
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Any amino acid
<220> FEATURE:
<221> NAME/KEY: MOD_RES
<222> LOCATION: (6)..(6)
<223> OTHER INFORMATION: Any amino acid

<400> SEQUENCE: 14

Arg His Gly Xaa Arg Xaa Pro
1               5

<210> SEQ ID NO 15
<211> LENGTH: 3
<212> TYPE: PRT
<213> ORGANISM: Artificial Sequence
```

```
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (3)..(3)
<223> OTHER INFORMATION: Ser or Thr

<400> SEQUENCE: 15

Asn Xaa Xaa
1

<210> SEQ ID NO 16
<211> LENGTH: 7
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (2)..(3)
<223> OTHER INFORMATION: a, c, t, g, unknown or other

<400> SEQUENCE: 16 rnnatgg                                                                    7

<210> SEQ ID NO 17
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
aagcttatga aattc                                                          15

<210> SEQ ID NO 18
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: CDS
<222> LOCATION: (13)..(24)

<400> SEQUENCE: 18
aagctttccg cc atg gcg aaa ttc                                             24
              Met Ala Lys Phe
              1

<210> SEQ ID NO 19
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Met Ala Lys Phe
1
```

```
<210> SEQ ID NO 20
<211> LENGTH: 33
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Glu Leu Lys Gln Ile Asn Val Ile Phe Arg His Gly Asp Arg Ile Pro
1               5                   10                  15

Asp Glu Lys Asn Glu Met Tyr Pro Lys Lys Leu Glu Gly Trp Thr Asp
            20                  25                  30

Lys

<210> SEQ ID NO 21
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Phe Val Asp Glu Ser Ala Asn Asn Leu Ser Ile Glu Glu Ile Asp Phe
1               5                   10                  15

Val Lys

<210> SEQ ID NO 22
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Leu Gln Gln Trp Asn Glu Asp Leu Asn Trp Gln Pro Ile Ala Thr Lys
1               5                   10                  15

<210> SEQ ID NO 23
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Gly Lys Tyr Glu Phe Ser Lys Arg
1               5

<210> SEQ ID NO 24
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Tyr Asn Ile Phe Ala Gly Thr Trp Lys
1               5
```

```
<210> SEQ ID NO 25
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Leu Tyr Gly Gly Pro Leu Leu Arg Asp Asn Tyr Val Gly Asp Glu Arg
1               5                   10                  15

<210> SEQ ID NO 26
<211> LENGTH: 86
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Asp Ile Thr Thr Pro Lys Asp Tyr Tyr Ile Tyr His Thr Leu Val
1               5                   10                  15

Ala Glu Asn Glu Tyr Ser Ser Cys Ile Ile Met Glu Tyr His Asn Ile
            20                  25                  30

Glu Gly Thr His Tyr Val Lys Ile Val Tyr Tyr Leu Gly Ile Pro Ser
        35                  40                  45

Glu Ala Arg Glu Leu Gln Leu Pro Gly Cys Glu Val Leu Cys Pro Leu
    50                  55                  60

Glu Lys Tyr Leu Gln Leu Ile Glu Asn Val Ile Pro Ser Asn Glu Glu
65                  70                  75                  80

Leu Ile Cys Asp Lys Arg
                85

<210> SEQ ID NO 27
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Glu Leu Lys Gln Ile Asn Val Ile Phe Arg His Gly Asp Arg Ile Pro
1               5                   10                  15

Asp Glu Lys Asn Glu Met Tyr Pro Lys
            20                  25

<210> SEQ ID NO 28
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Gly Lys Tyr Glu Phe Ser Lys
1               5

<210> SEQ ID NO 29
<211> LENGTH: 6
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 29

Lys Leu Glu Glu Trp Thr
1               5

<210> SEQ ID NO 30
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Ile Thr Thr Pro Lys Asp Tyr Tyr Tyr Ile Tyr His Thr Leu Val Ala
1               5                   10                  15

Glu

<210> SEQ ID NO 31
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Leu Tyr Gly Gly Pro Leu Leu Arg
1               5

<210> SEQ ID NO 32
<211> LENGTH: 85
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Glu Tyr Ser Ser Cys Ile Ile Met Glu Tyr His Asn Ile Glu Gly Thr
1               5                   10                  15

His Tyr Val Lys Ile Val Tyr Tyr Leu Gly Ile Pro Ser Glu Ala Arg
            20                  25                  30

Glu Leu Gln Leu Pro Gly Cys Glu Val Leu Cys Pro Leu Glu Lys Tyr
        35                  40                  45

Leu Gln Leu Ile Glu Asn Val Ile Pro Ser Asn Glu Glu Leu Ile Cys
    50                  55                  60

Asp Lys Arg Phe Val Asp Glu Ser Ala Asn Asn Leu Ser Ile Glu Glu
65                  70                  75                  80

Ile Asp Phe Val Lys
                85

<210> SEQ ID NO 33
<211> LENGTH: 392
<212> TYPE: PRT
<213> ORGANISM: Drosophila melanogaster

<400> SEQUENCE: 33

Gln Leu Lys Phe Val His Val Ile Tyr Arg His Gly Asp Arg Thr Pro
1               5                   10                  15

Val Asp Pro Tyr Pro Thr Asp Pro Trp Gly Asp Arg Lys Phe Trp Pro
```

-continued

```
                 20                  25                  30
Thr Gly Trp Gly Asp Leu Thr Asn Leu Gly Lys Gln Glu His Tyr Asp
         35                  40                  45

Leu Gly Lys Trp Leu Arg Asn Arg Tyr Ser Asn Leu Leu Pro Pro Ile
 50                  55                  60

Tyr Ser Asn Glu Asn Ile Tyr Val Gln Ser Thr Asp Val Asp Arg Thr
65                  70                  75                  80

Leu Met Ser Ala Gln Ser Asn Leu Ala Gly Leu Tyr Glu Pro Gln Gly
                 85                  90                  95

Glu Asp Ile Trp Asn Thr Asp Ile Asn Trp Gln Pro Ile Pro Ile His
            100                 105                 110

Thr Ser Pro Glu Arg Glu Asp Pro Ile Leu Ala Ala Lys Ala Pro Cys
        115                 120                 125

Pro Ala Tyr Asp Tyr Glu Leu Ala Ser Leu Glu Ser Ser Pro Glu Phe
        130                 135                 140

Lys Ala Leu Thr Glu Lys His Arg Asn Leu Phe Ala Tyr Leu Ser Glu
145                 150                 155                 160

Lys Gly Arg Pro Val Lys Thr Phe Ile Asp Ala Gln Tyr Leu Asn
                165                 170                 175

Asn Thr Leu Phe Ile Glu Asn Leu Tyr Asn Met Thr Leu Pro Lys Trp
            180                 185                 190

Thr Lys Lys Val Tyr Gly Arg Glu Glu Leu Thr Tyr Val Ser Asn Phe
        195                 200                 205

Ala Phe Ala Ile Ser Ser Tyr Thr Arg Lys Leu Ala Arg Leu Lys Ala
        210                 215                 220

Gly Pro Leu Leu Lys Asp Ile Phe Gln Arg Phe Lys Glu Lys Ser Ser
225                 230                 235                 240

Gly Ser Leu Lys Pro Asp Arg Ser Met Trp Val Tyr Ser Ala His Asp
                245                 250                 255

Thr Thr Val Ala Ser Val Leu Asn Ala Leu Lys Leu Phe Glu Leu His
            260                 265                 270

Ser Pro Pro Tyr Thr Ala Cys Ile Met Met Glu Leu Arg Val Asp Glu
        275                 280                 285

Thr Asn Thr Pro Leu Val Ser Ile Phe Tyr Lys Asn Thr Thr Ala Glu
        290                 295                 300

Pro Leu Pro Leu Asp Ile Pro Gly Cys Gly Pro Ser Cys Pro Leu Thr
305                 310                 315                 320

Lys Leu Met Asn Ile Tyr Glu Asp Val Leu Pro Val Asp Trp Glu Arg
                325                 330                 335

Glu Cys Lys Leu Ser Thr Met Met Thr Tyr Glu Glu Ala Asn Leu
            340                 345                 350

Gly Thr Ala Thr Gly Ile Leu Ile Leu Ile Val Ile Ala Leu Leu Phe
        355                 360                 365

Ala Ser Tyr Gly Leu Met Ile Tyr Tyr Arg Arg Asn Tyr Lys Leu
        370                 375                 380

Tyr Ser Ser Tyr Ser Gln Met Ala
385                 390

<210> SEQ ID NO 34
<211> LENGTH: 392
<212> TYPE: PRT
<213> ORGANISM: Drosophila melanogaster

<400> SEQUENCE: 34
```

```
Gln Leu Lys Phe Val His Val Ile Tyr Arg His Gly Asp Arg Thr Pro
1               5                   10                  15

Val Asp Pro Tyr Pro Thr Asp Pro Trp Gly Asp Arg Lys Phe Trp Pro
                20                  25                  30

Thr Gly Trp Gly Asp Leu Thr Asn Leu Gly Lys Gln Glu His Tyr Asp
            35                  40                  45

Leu Gly Lys Trp Leu Arg Asn Arg Tyr Ser Asn Leu Leu Pro Pro Ile
        50                  55                  60

Tyr Ser Asn Glu Asn Ile Tyr Val Gln Ser Thr Asp Val Asp Arg Thr
65                  70                  75                  80

Leu Met Ser Ala Gln Ser Asn Leu Ala Gly Leu Tyr Glu Pro Gln Gly
                85                  90                  95

Glu Asp Ile Trp Asn Thr Asp Ile Asn Trp Gln Pro Ile Pro Ile His
            100                 105                 110

Thr Ser Pro Glu Arg Glu Asp Pro Ile Leu Ala Ala Lys Ala Pro Cys
        115                 120                 125

Pro Ala Tyr Asp Tyr Glu Leu Ala Ser Leu Glu Ser Ser Pro Glu Phe
        130                 135                 140

Lys Ala Leu Thr Glu Lys His Arg Asn Leu Phe Ala Tyr Leu Ser Glu
145                 150                 155                 160

Lys Gly Gly Arg Pro Val Lys Thr Phe Ile Asp Ala Gln Tyr Leu Asn
                165                 170                 175

Asn Thr Leu Phe Ile Glu Asn Leu Tyr Asn Met Thr Leu Pro Lys Trp
            180                 185                 190

Thr Lys Met Val Tyr Gly Arg Glu Glu Leu Thr Tyr Val Ser Asn Phe
        195                 200                 205

Ala Phe Ala Ile Ser Ser Tyr Thr Arg Lys Leu Ala Arg Leu Lys Ala
210                 215                 220

Gly Pro Leu Leu Lys Asp Ile Phe Gln Arg Phe Lys Glu Lys Ser Ser
225                 230                 235                 240

Gly Ser Leu Lys Pro Asp Arg Ser Met Trp Val Tyr Ser Ala His Asp
                245                 250                 255

Thr Thr Val Ala Ser Val Leu Asn Ala Leu Lys Leu Phe Glu Leu His
            260                 265                 270

Ser Pro Pro Tyr Thr Ala Cys Ile Met Met Glu Leu Arg Val Asp Glu
        275                 280                 285

Thr Asn Thr Pro Leu Val Ser Ile Phe Tyr Lys Asn Thr Thr Ala Glu
        290                 295                 300

Pro Leu Pro Leu Asp Ile Pro Gly Cys Gly Pro Ser Cys Pro Leu Thr
305                 310                 315                 320

Lys Leu Met Asn Ile Tyr Glu Asp Val Leu Pro Val Asp Trp Glu Arg
                325                 330                 335

Glu Cys Lys Leu Ser Thr Met Met Thr Tyr Glu Glu Ala Asn Leu
            340                 345                 350

Gly Thr Ala Thr Gly Ile Leu Ile Leu Ile Val Ile Ala Leu Leu Phe
        355                 360                 365

Ala Ser Tyr Gly Leu Met Ile Tyr Tyr Arg Arg Arg Asn Tyr Lys Leu
        370                 375                 380

Tyr Ser Ser Tyr Ser Gln Met Ala
385                 390
```

<210> SEQ ID NO 35
<211> LENGTH: 392
<212> TYPE: PRT

<213> ORGANISM: Drosophila subobscura

<400> SEQUENCE: 35

| | | | | | | | | | | | | | | |
|---|---|---|---|---|---|---|---|---|---|---|---|---|---|---|
| Glu | Leu | Lys | Phe | Ala | His | Val | Ile | Phe | Arg | His | Gly | Asp | Arg | Thr | Pro |
| 1 | | | | 5 | | | | | 10 | | | | | 15 | |
| Val | Asp | Pro | Tyr | Pro | Thr | Asp | Pro | Trp | Asn | Asn | Arg | Lys | Phe | Trp | Pro |
| | | | 20 | | | | | 25 | | | | | 30 | | |
| Thr | Gly | Trp | Gly | Gln | Leu | Thr | Asn | Leu | Gly | Lys | Glu | Gln | His | Tyr | Glu |
| | | | 35 | | | | | 40 | | | | | 45 | | |
| Leu | Gly | Lys | Trp | Leu | Arg | Asn | Arg | Tyr | Lys | Ser | Leu | Leu | Gly | Ser | Arg |
| | 50 | | | | | 55 | | | | | 60 | | | | |
| Tyr | Thr | Asn | Glu | Asp | Ile | Phe | Val | Gln | Ser | Thr | Asp | Val | Asp | Arg | Thr |
| 65 | | | | | 70 | | | | | 75 | | | | | 80 |
| Leu | Met | Ser | Ala | Gln | Ser | Asp | Leu | Ala | Gly | Leu | Tyr | Glu | Pro | Gln | Gly |
| | | | | 85 | | | | | 90 | | | | | 95 | |
| Asp | Asp | Ile | Trp | Asn | Pro | Arg | Ile | Asp | Trp | Gln | Pro | Val | Pro | Val | His |
| | | | 100 | | | | | 105 | | | | | 110 | | |
| Thr | Val | Pro | Glu | Lys | Asp | Asp | Ser | Ile | Leu | Ala | Ala | Lys | Ala | Ser | Cys |
| | | | 115 | | | | | 120 | | | | | 125 | | |
| Pro | Ala | Tyr | Asp | Tyr | Glu | Leu | Ala | Thr | Leu | Glu | Ala | Ser | Ser | Glu | Phe |
| | 130 | | | | | 135 | | | | | 140 | | | | |
| Gln | Ala | Leu | Tyr | Val | Arg | Tyr | Arg | Glu | Leu | Leu | Ser | Tyr | Leu | Thr | Gln |
| 145 | | | | | 150 | | | | | 155 | | | | | 160 |
| Asn | Ser | Gly | Arg | His | Val | Lys | Ser | Phe | Ile | Asp | Ala | Gln | Tyr | Leu | Asn |
| | | | | 165 | | | | | 170 | | | | | 175 | |
| Asn | Thr | Leu | Phe | Ile | Glu | Lys | Leu | Tyr | Asn | Met | Thr | Leu | Pro | Val | Trp |
| | | | 180 | | | | | 185 | | | | | 190 | | |
| Ala | Glu | Lys | Val | Tyr | Gly | Lys | Glu | Glu | Leu | Thr | Tyr | Val | Ser | Asn | Phe |
| | | | 195 | | | | | 200 | | | | | 205 | | |
| Ala | Phe | Ser | Ile | Ala | Thr | Phe | Thr | Arg | Ser | Met | Ala | Arg | Leu | Lys | Thr |
| | 210 | | | | | 215 | | | | | 220 | | | | |
| Gly | Pro | Leu | Leu | Lys | Asp | Ile | Phe | Glu | Arg | Phe | Asp | Lys | Lys | Leu | Asn |
| 225 | | | | | 230 | | | | | 235 | | | | | 240 |
| Asn | Gln | Leu | Lys | Pro | Asp | Arg | Ser | Leu | Trp | Ile | Tyr | Ser | Ala | His | Asp |
| | | | | 245 | | | | | 250 | | | | | 255 | |
| Thr | Thr | Ile | Ala | Asn | Val | Leu | Asn | Ser | Leu | Lys | Leu | Phe | Glu | Leu | His |
| | | | 260 | | | | | 265 | | | | | 270 | | |
| Ser | Pro | Pro | Tyr | Ala | Ala | Cys | Ile | Met | Leu | Glu | Met | Arg | Val | Asp | Asp |
| | | | 275 | | | | | 280 | | | | | 285 | | |
| Ser | Asn | Thr | Pro | Leu | Val | Ser | Val | Phe | Tyr | Lys | Asn | Thr | Thr | Ala | Glu |
| | 290 | | | | | 295 | | | | | 300 | | | | |
| Pro | Leu | Pro | Leu | Asp | Ile | Pro | Gly | Cys | Gly | Leu | Ser | Cys | Pro | Leu | Lys |
| 305 | | | | | 310 | | | | | 315 | | | | | 320 |
| Thr | Leu | Val | Lys | Leu | Tyr | Gln | Asp | Val | Leu | Pro | Gly | Asn | Trp | Glu | Arg |
| | | | | 325 | | | | | 330 | | | | | 335 | |
| Glu | Cys | Lys | Arg | Ser | Thr | Met | Met | Thr | Tyr | Glu | Glu | Ala | Asn | Leu |
| | | | 340 | | | | | 345 | | | | | 350 | | |
| Gly | Ala | Ala | Thr | Gly | Ile | Leu | Ile | Phe | Ile | Ile | Thr | Val | Leu | Leu | Cys |
| | | | 355 | | | | | 360 | | | | | 365 | | |
| Ala | Ser | Tyr | Gly | Leu | Met | Val | Tyr | Tyr | Arg | Arg | His | Tyr | Asn | Leu |
| | 370 | | | | | 375 | | | | | 380 | | | | |
| Tyr | Thr | Ser | Tyr | Ser | Gln | Met | Ala |
| 385 | | | | | 390 | | |

<210> SEQ ID NO 36
<211> LENGTH: 356
<212> TYPE: PRT
<213> ORGANISM: Drosophila melanogaster

<400> SEQUENCE: 36

Thr Leu Lys Leu Val His Val Leu Phe Arg His Gly Pro Arg Thr Pro
1               5                   10                  15

Val Ser Thr Tyr Pro Asn Asp Pro Tyr Ile Asn Glu Thr Tyr Glu Pro
            20                  25                  30

Phe Gly Trp Gly Ala Leu Thr Asn Gly Ala Lys Val Glu Leu Tyr Lys
        35                  40                  45

Ile Gly Lys Gln Leu Arg Gln Arg Tyr Lys Asp Phe Leu Pro Ala Tyr
    50                  55                  60

Tyr Gln Pro Asp Ala Ile Arg Ala Gln Ser Ser Glu Ser Pro Arg Thr
65                  70                  75                  80

Leu Met Ser Met Gln Met Val Leu Ala Gly Leu Phe Pro Pro Glu Asn
                85                  90                  95

Thr Pro Met Glu Trp Asn Gln Leu Leu Asn Trp Gln Pro Ile Pro Ile
            100                 105                 110

Val Met Glu Pro Glu Thr Asp Val His Ile Arg Met Lys Ala Pro
        115                 120                 125

Cys Pro Arg Tyr Asp Glu Ser Val Leu Glu Val Ile Glu Leu Pro Glu
    130                 135                 140

Val Lys Lys Leu His Ala Glu Ser Ser Asp Leu Leu Arg Glu Leu Thr
145                 150                 155                 160

Thr His Thr Gly Leu Asn Ile Thr His Ala His Asp Val Thr Asn Val
                165                 170                 175

Phe Ile Thr Leu Leu Cys Glu Gln Thr Phe Gly Leu Gln Leu Pro Ser
            180                 185                 190

Trp Thr Asn Asp Tyr Phe Pro Glu Lys Met Leu Pro Leu Ala Glu Lys
        195                 200                 205

Ser Tyr Val Tyr Asp Ala Tyr Thr Thr Glu Gln Arg Lys Met Lys Gly
    210                 215                 220

Gly Phe Phe Val Glu Leu Leu Leu Lys Gln Met Gln Asp Arg Ile Ser
225                 230                 235                 240

Gly Ala Leu Lys Pro Ala Asn Arg Lys Met Phe Leu Ser Cys Gly His
                245                 250                 255

Asp Trp Thr Ile Thr Asn Val Leu Ser Ala Leu Asn Val Trp Glu Ala
            260                 265                 270

Gln Met Pro Arg Phe Ser Ser Leu Ile Ala Phe Glu Leu His Gln Asn
        275                 280                 285

Pro Gln Thr Gly Glu Tyr Phe Leu Glu Ile Tyr Phe Gln Asn Asp Pro
    290                 295                 300

His Lys Glu Pro Gln Gln Leu Gln Ile Pro Gly Cys Glu Lys Gln Cys
305                 310                 315                 320

Pro Ile Gly Lys Leu Leu Glu Leu Thr Lys Asp Ile Ile Pro Asp Ala
                325                 330                 335

Pro Tyr Ala Glu Leu Cys Lys Ala Lys Gly Thr Gln Gly Gly Ala Lys
            340                 345                 350

Ile Ser Tyr His
        355

<210> SEQ ID NO 37

```
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Gln Ile Asn Val Ile Phe Arg
1               5

<210> SEQ ID NO 38
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Asp Pro Tyr Leu Tyr Tyr Asp Phe Tyr Pro Leu Glu Arg
1               5                   10

<210> SEQ ID NO 39
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Glu Tyr Gln Leu Gly Gln Phe Leu Arg
1               5

<210> SEQ ID NO 40
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

His Met Leu Asp Val Val Ser Gly Thr Gln Lys
1               5                   10

<210> SEQ ID NO 41
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Ile Val Tyr Tyr Leu Gly Ile Pro Ser Glu Ala Arg
1               5                   10
```

CLONING OF HONEY BEE ALLERGEN

CROSS-REFERENCE TO RELATED APPLICATION

This application claims the benefit of and claims priority under 35 U.S.C. §119 (e) to U.S. Provisional Application No. 60/635,479, filed Dec. 14, 2004, which application is herein incorporated by reference in its entirety.

INCORPORATION OF SEQUENCE LISTING

The file named "19695-003-Seq-d.txt," which is 28,695 bytes in size (measured in MS-DOS) and which was created on Mar. 1, 2010, is herein expressly incorporated by reference.

The present invention relates to a nucleic acid encoding a polypeptide capable of binding to IgE from subjects allergic to venom of an insect from the order Hymenoptera having a homology of more than 70% to the amino acid sequence of SEQ ID NO: 2, which is the honey bee allergen Api m3 (acid phosphatase). The invention further relates to expression vectors, host cells and polypeptides encoded by the nucleic acid, as well as diagnostic and pharmaceutical uses thereof.

It has long been recognised that allergies against insect venoms are relatively common. 4-5% of the German population react allergic to insect venoms. In Europe the relevant stinging insects are honey bees (*Apis mellifera*), wasps (*Vespula* spp.), bumble bees (*Bombus* spp.), hornets (*Vespa crabo*), midges, and horse flies (Ref.1,2). Bees, bumble bees, wasps, and hornets belong to the order Hymenoptera.

These social insects do not normally attack people, but will sting them in self defence if disturbed. Once stung, if the stinger remains in the skin, a honey bee is responsible, while, if no stinger is present, a wasp is likely to be the culprit. The female worker honey bee carries the stinger and dies soon after discharging a sting.

If a bee stings a vertebrate, the stinger will be detached from the insect, but the venom sack will still be attached to the stinger and if not removed, the whole venom volume (up to 50 µl) will be injected into the victim. Wasps can retract the stinger, and only inject about 20 µl venom.

The differences in stinging behaviour are based on natural evolution. Bees collect nectar, whereas wasps and hornets are insect hunters. Therefore, bees need to protect the hive, even against vertebrates like mice or larger animals. The insect dies upon the sting, but will inject the maximum volume of venom, if the stinger is not removed. Wasps and hornets do not have such natural enemies.

Since it is easy to obtain sufficient quantities of material, honey bee venom has been well studied. Honey bee venom contains at least 18 active substances. Melittin, the most prevalent substance, is one of the most potent anti-inflammatory agents known (100 times more potent than hydrocortisone). Adolapin is another strong anti-inflammatory substance, and inhibits cyclooxygenase; it thus has analgesic activity as well. Apamin inhibits complement C3 activity, and blocks calcium-dependent potassium channels, thus enhancing nerve transmission. Other substances, such as Compound X, Hyaluronidase, Phospholipase A2, Histamine, and Mast Cell Degranulating Protein (MSDP), are involved in the inflammatory response to venom, with the softening of tissue and the facilitation of flow of the other substances. Finally, there are measurable amounts of the neurotransmitters Dopamine, Norepinephrine and Serotonin. The water content varies between 55-70%. The pH range is between 4.5-5.5. A summary of the components of bee venom is given in table 1 (Ref. 3,4).

TABLE 1

| Bee venom components | | |
|---|---|---|
| Component type | name | % weight of dry mass |
| Proteins | Phospholipase A2 (Api m 1) | 10-12 |
|  | Hyaluronidase (Api m 2) | 1-3 |
|  | Phosphatase, Glucosidase | 1-2 |
| Peptides | Melittin (Api m 4) | 50-55 |
|  | Secapin, MCD-peptide | 1.5-4 |
|  | Tertiapamin, Apamin, Procamin | 2-5 |
|  | Other small peptides | 13-15 |
| Biogene amines | Histamine | 0.5-2 |
|  | Dopamine | 0.2-1 |
|  | Norepinephrine | 0.1-0.5 |
|  | Sugars (Glucose, Fructose) | 2 |
| Phospholipids |  | 5 |
| Amino acids |  | — |
| Volatile substances | Pheromones | 4-8 |
| Minerals |  | 3-4 |

The LD50 dose, i.e., the amount of bee venom which causes 50% of the tested individuals to die, is 6 mg venom/kg body weight for mice and rats. This equals 40 stings/kg body weight. For hornets, this factor is around 154-180 stings/kg body weight. Bee venom is 1.7-1.5 more effective than those of hornets (Ref. 5,6).

Honey bees and wasps of the Hymenoptera order are by far the most frequent cause of serious allergic reactions. Normally, at least more than 50 stings of a bee per children or 100 per adult are necessary to induce life threatening conditions (see above). In case of allergic persons, one sting can be enough to cause death by adverse immunological reactions.

This type of allergy is mediated by IgE antibodies which react to venom components. The possibility, therefore, exists that desensitisation therapy by repeated and progressively increased doses of bee venom components would be successful. Several polypeptides from bee venom have been cloned and expressed as recombinant molecules (Ref. 7-16). One component of bee venom, acid phosphatase, is one of the more potent allergic proteins (Ref. 17). Until now, no information about the complete gene sequence has been published and only initial studies on protein level have been made (Ref. 18-20, 27).

Barboni et al. (Ref. 19) describe two different proteins with acid phosphatase activity from honey bee venom, having a molecular weight of 45 and 96 kDa. Enzymatic activity is partly lost during purification in the gel filtration step. Other publications (Ref. 18, 20, 27) report contrasting data, teaching different fragments of the protein and the corresponding nucleic acid, and coming to different conclusions about the family of phosphatases that honey bee venom acid phosphatase might belong to, either prostatic phosphatases or lysosomal phosphatases. Soldatova et al. (Ref. 18) describe the incomplete cloning of a partial cDNA possibly encoding an acid phosphatase from honey bee venom. They report difficulties in cloning and obtaining the full length sequence and do not teach the sequence they seem to have cloned.

In light of the prior art, the person skilled in the art is therefore faced with the problem of providing a nucleic acid suitable for recombinant production of acid phosphatase (api m3) from the venom of an insect from the order Hymenoptera, in particular the honey bee, which can be used in such desensitisation therapy as well as in diagnostic tests for the detection of allergy.

This problem is solved by the subject matter of the claims.

In particular, the present invention provides a nucleic acid encoding a polypeptide capable of binding to IgE from subjects allergic to venom of an insect from the order Hymenoptera wherein the polypeptide has a homology of more than 70% to the amino acid sequence of SEQ ID NO: 2 (note: "SEQ ID NO" relates to code <400>in the attached sequence listing under WIPO standard ST.25).

Preferentially, the degree of homology to the amino acid sequence of SEQ ID NO: 2 is more than 75%, more than 80%, more than 85%, more than 90%, more than 95% or more than 99%. The sequence homology is determined using the clustal computer program available from the European Bioinformatics Institute (EBI). Most preferentially, the polypeptide encoded by the nucleic acid has the amino acid sequence of SEQ ID NO: 2. This polypeptide is designated Api m 3. In particular, the nucleic acid comprises or has the nucleotide sequence of SEQ ID NO: 1.

In the context of the present invention, the terms "polypeptide" and "protein" are used interchangeably, without any limitation as to the number of amino acids linked. The polypeptides may also comprise non-naturally occuring amino acids.

Throughout this specification, the polypeptides encoded by the nucleic acid of the invention have to be capable of binding to IgE from subjects allergic to venom of an insect from the order Hymenoptera.

Following unsuccessfull attempts to clone the full length sequence of Api m 3 following the common deduced primer strategy (cf. Soldatova et al., 2000) based on the peptide fragments found by Hoffmann, 1996, and their postulated sequence (Hoffmann, 1996). A completely different approach was chosen in the present invention. Using nucleic acid sequences derived from the peptide sequences published by Hoffman, small virtual probes of partial deduced sequences were constructed, which were used to scan the published bee genome for targets. Two regions on different truncated chromosome 16 sequences matched the probes. Scanning of these regions with bioinformatic tools revealed possible open reading frames and gene sequences. Scanning for a potential sequence cleavage site led to the putative N-terminus of the Api m 3 gene. Primers were then designed according to the proposed protein N- and C-terminus. These primers were used to amplify the gene from bee venom gland cDNA synthesized from total RNA with oligodT(20) primers. The amplification was successful and resulted in a DNA fragment of the expected size. The identity of the DNA was verified by sequencing, molecular weight calculation and alignment to the homologous acid phosphatases of human as well as rat sequences and the proposed peptide fragments. The protein identity was also verified.

From the resulting full length cDNA sequence, it is clear the classical approach had to fail, as Hoffman erred in several points. For example, he chose an incorrect alignment of the peptide fragments (cf. FIG. 5), erroneously thought that several peptides that are in fact separated by other peptides were contigous, and postulated existence of a fragment that does not belong to the acid phosphatase. In fact, using primers based on peptides 1 and 7, as proposed by Hoffman, one would expect to amplify a short fragment covering only the peptide sequence around amino acids 200 and 230 of the consensus sequence.

The social insects from the order Hymenoptera that commonly interact with man are members of the superfamilies Apoidea and Vespoidea, bees and wasps (Ref. 20). The Vespoidea include the social wasps and hornets, *Vespidae*, as well as ants, *Formicidae*. Important wasps comprise yellow-jackets of the genus *Vespula*, hornets of the genera *Dolichovespula* and *Vespa* and paper wasps of the genus *Polistes*. Bees comprise, e.g., honey bees, *Apis mellifera*, and bumble bees of the species *Bombus terrestris*. In the context of the present invention, an insect from the order Hymenoptera can be from any of these species, but according to a particular embodiment, the insect is a bee from the genus *Apis*. Most preferably, the bee is the honey bee, *Apis mellifera*.

Other species from the order Hymenoptera produce similar allergens with antigenic cross reactivity and a high degree of amino acid homology (Ref. 24-26). Thus the present invention not only extends to the Api m3 allergen from *Apis mellifera* but also to homologous Hymenoptera allergens.

In particular, the polypeptides encoded by the nucleic acids of the invention have to be capable of binding to IgE from subjects allergic to venom of *Apis mellifera*. The subjects are commonly reactive to the Api m3 antigen, acid phosphatase from bee venom. For the purpose of testing, serum or purified IgE from such allergic subjects are contacted with the polypeptide, and specific binding of the polypeptide to the antibodies is detected. Such a test can, e.g., be an ELISA. For verifying the reactivity of the polypeptides with IgE antibodies, serum or IgE from several subjects are pooled, preferentially, from 5 to 20 subjects.

The nucleic acids of the invention can be either DNA or RNA.

In one embodiment, the invention also provides a nucleic acid, which is a fragment having a length of more than 255 nucleotides of a nucleic acid encoding a polypeptide having a homology of more than 70% to the amino acid sequence of SEQ ID NO: 2, wherein the fragment encodes a polypeptide capable of binding to IgE from subjects allergic to venom of an insect from the order Hymenoptera. Preferably, the nucleic acid is a fragment having a length of more than 255, more preferably of more than 600, more than 700 or more than 800 nucleotides of a nucleic acid encoding a polypeptide having the amino acid sequence of SEQ ID NO: 2.

In another embodiment, a nucleic acid fragment (polynucleotide) is provided that comprises at least 15 contiguous nucleotides of the nucleic acid encoding a polypeptide having the amino acid sequence of SEQ ID NO: 2, wherein the polynucleotide is selected from the group consisting of nucleotides 78 to 299, 348 to 437, 459 to 476, 555 to 671, 696 to 830 or 1086 to 1121 of said nucleic acid, wherein the numbering corresponds to the region encoding said polypeptide. Specifically, said nucleic acid has the nucleotide sequence shown in SEQ ID NO: 1. Preferentially, the nucleotides are from the region of nucleotides 555 to 671 or 696 to 830. Alternatively, the nucleic acids encode polypeptides that are capable of binding to IgE from subjects allergic to venom of an insect from the order Hymenoptera, and comprise at least 15, preferably at least 18, 21, 24, 27, 30, 45, 60 or more nucleotides of a nucleic acid more than 70%, more than 80% or more than 90% homologous or identical to the nucleic acid shown in SEQ ID NO: 1, except for the nucleic acids from the group consisting of nucleotides 1 to 104, 189 to 142, 300 to 347, 426 to 449, 504 to 530, 672 to 719 and 774 to 1031 of the nucleic acid shown in SEQ ID NO: 1 or except for the nucleic acids encoding the polypeptides shown in FIG. 5. Additionally, such nucleic acids consisting of nucleotides 1 to 77, 438 to 458, 477 to 494, 504 to 554, 672 to 695, and 831 to 1085 of the nucleic acid shown in SEQ ID NO: 1 are provided.

Preferentially, the nucleic acid comprises 15 to 240, 15 to 90, 18 to 60, 21 to 30, more preferably at least 18, 21, 24, 27, 30, 60, 90 or more contiguous nucleotides from the above regions.

Alternatively, a nucleic acid is provided which encodes a polypeptide having more than 70% homology to the polypeptide encoded by said at least 15 contiguous nucleotides, wherein the polypeptide is capable of binding to IgE from subjects allergic to venom of an insect from the order Hymenoptera. In particular, this polypeptide comprises at least 5, preferably at least 6, 7, 8, 9, 10, 15, 20 or more amino acids of a polypeptide more than 70%, more than 80% or more than 90% homologous or identical to a polypeptide selected from the group consisting of amino acid 26 to 99, 116 to 145, 153 to 158, 185 to 223, 232 to 276 or 362 to 373 of the polypeptide shown in SEQ ID NO: 2. Alternatively, the polypeptides encoded by the nucleic acids are capable of binding to IgE from subjects allergic to venom of an insect from the order Hymenoptera, and comprise at least 5, preferably at least 6, 7, 8, 9, 10, 15, 20 or more amino acids of a polypeptide more than 70%, more than 80% or more than 90% homologous or identical to the polypeptide shown in SEQ ID NO: 2, except for the polypeptides from the group consisting of amino acids 1 to 34, 63 to 80, 100 to 115, 142 to 149, 168 to 176, 224-239 and 258 to 343 of the polypeptide shown in SEQ ID NO: 2 or except for the polypeptides shown in FIG. 5. Additionally, such polypeptides consisting of amino acids 1 to 25, 146 to 152, 159 to 164, 168 to 184, 224 to 231, and 277 to 361 are encoded by the nucleic acids.

In one embodiment, the invention also provides a polypeptide encoded by a nucleic acid of the invention. Preferentially, the polypeptide is a full length acid phosphatase from the venom of an insect from the order Hymenoptera. In particular, the polypeptide has an homology of more than 70%, more than 75%, more than 80%, more than 85%, more than 90%, more than 95% or more than 99% to the amino acid sequence of SEQ ID NO: 2. Most preferred is a polypeptide having the amino acid sequence of SEQ ID NO: 2. Although not essential, it is preferred that the polypeptide has acid phosphatase activity. This activity can be tested, e.g., according to the method described in Ref. 19.

Alternatively, the polypeptide is a fragment of the full length protein capable of binding to IgE from subjects allergic to venom of an insect from the order Hymenoptera having a length of more than 85, more than 200 or more than 250 amino acids. Other fragments are provided, wherein the polypeptides are capable of binding to IgE from subjects allergic to venom of an insect from the order Hymenoptera, and comprise at least 5, preferably at least 6, 7, 8, 9, 10, 15, 20 or more amino acids of a polypeptide more than 70%, more than 80% or more than 90% homologous or identical to a polypeptide selected from the group consisting of amino acid 26 to 99, 116 to 145, 153 to 158, 185 to 223, 232 to 276 or 362 to 373 of the polypeptide shown in SEQ ID NO: 2. Alternatively, the polypeptides are capable of binding to IgE from subjects allergic to venom of an insect from the order Hymenoptera, and comprise at least 5, preferably at least 6, 7, 8, 9, 10, 15, 20 or more amino acids of a polypeptide more than 70%, more than 80% or more than 90% homologous or identical to the polypeptide shown in SEQ ID NO: 2, except for the polypeptides from the group consisting of amino acids 1 to 34, 63 to 80, 100 to 115, 142 to 149, 168 to 176, 224-239 and 258 to 343 of the polypeptide shown in SEQ ID NO: 2 or except for the polypeptides shown in FIG. 5. Additionally, such polypeptides consisting of amino acids 1 to 25, 146 to 152, 159 to 164, 168 to 184, 224 to 231, and 277 to 361 are provided.

Preferably, the polypeptide of the invention is recombinantly expressed. This has the advantage, e.g., that the polypeptide can be expressed as a fusion protein linked to an additional polypeptide. For example, the polypeptide or fusion protein is attached to a signal sequence ensuring its secretion into the extracellular space or supernatant of the cultured cells, where appropriate. Due to novel techniques in molecular biology, the use of recombinant proteins in therapy and diagnostics is expected to increase the efficiency and diagnostic value in these medical applications (Ref. 21-23).

Depending on the host cell producing the recombinant protein, the protein is glycosylated (after expression in mammalian or yeast cells) or non-glycosylated (after expression in bacterial cells). The glycosylation pattern can vary depending on the host cell used, and can thus differ from the glycosylation pattern of natural acid phosphatase isolated from bee venom. In one alternative, the glycosylation pattern is identical to the glycosylation pattern of acid phosphatase isolated from bee venom. Glycosylation can have profound effects on the binding of specific antibodies.

When expressed in bacterial cells, the polypeptide of the invention lacks glycosylation. The protein thus differs from the native protein in respect to epitope presentation, and potentiality for folding and functionality. It was shown that carbohydrates can represent IgE epitopes and contribute to observed non-specific cross-reactivity of allergens, e.g., between bee and wasp proteins, due to similar features of the carbohydrate chains (Huby et al., Tox Sci 55: 235-246, 2000; Tretter et al., Int. Arch. Allergy Immunol. 102: 259-266, 1993; Hemmer et al., Cli. Exp. Allergy 34: 460-460, 2004). The cross-reactivity is one reason for false positive results in in vitro immunological tests (Petersen A., Mundt C., J Chromat B 756, 141-150, 2001). Expression of the non-glycosylated polypeptide eliminates these false positives, and can therefore be used to advantage in diagnostic and therapeutic applications.

The glycosylation pattern in eukaryotic cells other than insect cells, e.g., in mammalian cells, also varies from the glycosylation pattern of the native protein (Jenkins et al., Nat. Biotech. 14: 975-981, 1996). Even in insect cells, the glycosylation pattern is likely to be different due to overexpression of the protein.

Sequence analysis of Api m 3 shows that the protein comprises three putative glycosylation sites of the sequence Asn-Xaa-Ser/Thr (SEQ ID NO: 15). In one embodiment, the polypeptides of the invention comprise mutated glycosylation sites instead of glycosylation sites. In particular, in a mutated glycosylation site, the Asparagine (Asn) in the glycosylation site(s) can be exchanged against any other amino acid, preferably against Glutamine (Gln) (Elbein A.D. et al., 1991, Trends Biotechnol. 9(10):346-352). Alternatively, in a mutated glycosylation site, the Serine (Ser) can be exchanged against another amino acid or deleted. Accordingly, the invention also provides a nucleic acid encoding a polypeptide of the invention comprising at least one, preferably 2, or 3 mutated glycosylation sites instead of glycosylation sites. Most preferably, all glycosylation sites are mutated.

The present invention also relates to an expression vector comprising a nucleic acid of the invention operationally linked to an expression control sequence. In one alternative, the nucleic acid is linked in frame to a nucleic acid encoding an additional polypeptide, so the expression vector can be used for expression of a fusion protein. The additional polypeptide can be selected from the group comprising a poly-Histidine tag (His tag), glutathione-S-transferase, β-galactosidase, a cytokine, and an IgG-Fc. In particular, tags that simplify purification of the recombinant protein, e.g., a His tag, are employed. Such a tag may be cleaved off after purification of the protein.

Alternatively, it can be beneficial for therapeutic applications to express the polypeptide of the invention linked to a therapeutic polypeptide, e.g. a cytokine. For example, a fusion protein with a cytokine enhancing $T_H1$ and downregulating $T_H2$ responses or inducing class switch to IgG, such as IFN-γ, IL-10, IL-12 or TGF-β, can improve efficiency of desensitisation. If the expression vector is used for gene therapy, it is envisaged to use sequences rich in CpG (unmethylated cytosine guanidine dinucleotides), which promote $T_H1$ responses. Additionally or alternatively, the polypeptide of the invention can be linked to another polypeptide or protein, such as in the form of a fusion protein or as separate proteins expressed by the same vector. Preferably, the further polypeptides or proteins are other Hymenoptera venom proteins or antigenic fragments thereof.

The expression vector can be suitable for expression in different cell types, such as bacterial, yeast or mammalian cells. Preferentially, the vector is suitable for expression in insect cells, e.g., HighFive insect cells (Invitrogen, Karlsruhe, Germany). Alternatively, especially for gene therapy applications, the vector is suitable for expression in human cells. In this context, the expression of the encoded polypeptide can be directed by the choice of a suitable expression control sequence, e.g., an expression control sequence mainly or specifically operational in different cell types, such as lymphoid cells, for example dendritic cells, B cells or macrophages.

In one embodiment of the invention, the expression vector is pIB/V5-His (Invitrogen, Karlsruhe, Germany, Invitrogen Manual: InsectSelect BSD System with pIB/V5-His, Version G, 30 May 2003).

In particular, the vector can be pIB/Mel opt-H1O-Api m3, comprising the Api m3 cDNA sequence (SEQ ID NO: 1), which was modified to facilitate isolation and purification. A melittin signal sequence for secretion of the recombinant protein was added and the Kozak sequence was optimised for higher expression rates in insect cells (see FIG. 4 and Example 2). Alternatively, other signal sequences can be used for secretion of the protein. The expression vector can also be a different plasmid or a viral, e.g., baculoviral or adenoviral, vector. The expression vector further comprises a stop codon and a polyadenylation signal.

The present invention further relates to a host cell comprising said expression vector. This host cell can be a bacterial, yeast or mammalian cell, in particular an insect cell.

A method of producing a polypeptide encoded by a nucleic acid of the invention is provided, wherein the host cell is cultured under appropriate conditions for expression of said polypeptide and said polypeptide is purified. If the polypeptide is a fusion protein with a fusion partner facilitating purification, e.g., a His Tag or a GST-tag, a corresponding affinity column can be used for purification, e.g., a $Ni^{2+}$ or glutathione affinity column. For purification of an IgG fusion protein, a protein A or protein G column is suitable.

The expression vector of the invention can be used for the preparation of a pharmaceutical composition for treating subjects allergic to the venom of an insect from the order Hymenoptera. Treatment regimens using gene therapy approaches to desensitisation are known in the state of the art (e.g., Ref. 28).

The invention thus also provides a method of treating subjects allergic to the venom of an insect from the order Hymenoptera comprising administering to a subject with such an allergy an expression vector of the invention. The expression vector can be administered directly, e.g., by intravenous, intramuscular or subcutaneous injection, gene gun or together with cells taken from the subject which were transfected ex vivo.

As used herein, "subject" encompasses human subjects (patients), grown-ups as well as children, and animals.

A pharmaceutical composition comprising an expression vector of the invention, and, optionally, comprising a suitable adjuvant or expedient, can be employed for this purpose. In particular, this expression vector is rich in CpG sequences and/or encodes a cytokine which shifts the balance between $T_H1$ and $T_H2$ immune responses.

Alternatively, the polypeptide of the invention is used for the preparation of a pharmaceutical composition for treating subjects allergic to the venom of an insect from the order Hymenoptera. The invention thus provides a method of treating subjects allergic to the venom of an insect from the order Hymenoptera, comprising administering a polypeptide of the invention to a subject having such an allergy.

Desensitisation approaches are well known in the state of the art. In principle, repeated treatments of allergic individuals with suitable, normally progressively increased doses of allergen diverts the immune response to one dominated by T cells that favour the production of IgG and IgA antibodies over production of IgE antibodies. The IgG and IgA antibodies are thought to desensitise the subject by binding to the small amounts of allergen normally encountered, and preventing the allergen from binding to IgE. Desensitisation to insect or bee venom is almost universally successful (Ref. 29). Different protocols and time schedules can be used, from traditional protocols, rush protocols to ultrarush protocols (e.g., Ref. 30), all of which are incorporated herein by reference. The efficacy of such protocols can be evaluated by testing the adjustment of IgE and IgG (different isotypes) and/or IgA levels in the subject's blood or by challenging the subject in a controlled manner and determining the allergic response.

The polypeptide of the invention can be administered alone or combination with other allergens, e.g. other Hymenoptera venom proteins or fragments thereof. In particular, combinations with bee or Hymenoptera venom phospholipase A2, hyaluronidase, glucosidase and/or mellitin are suitable, as this therapy induces generation of IgG/IgA antibodies to several venom allergens and can thus lead to full protection. The identified bee allergens are shown in Table 2.

TABLE 2

Identified bee allergens

| Allergen | Common name | Size (processed) | Weight | SwissProt | Reference |
|---|---|---|---|---|---|
| Api m 1 | Phospholipase A2 | 134 aa | 15.2 kDa | P00630 | Kuchler et al 1989 |
| Api m 2 | Hyaluronidase | 349 aa | 40.7 kDa | Q08169 | Gmachl and Kreil 1993 |
| Api m 3 | Acid Phosphatase | nd | 45 kDa | — | Barboni et al 1987 |

TABLE 2-continued

Identified bee allergens

| Allergen | Common name | Size (processed) | Weight | SwissProt | Reference |
|---|---|---|---|---|---|
| Api m 4 | Melittin | 26 aa | 2.8 kDa | P01501 | Vlasak et al 1983 |
| Api m 5 | Allergen C | nd | 105 kDa | — | Hoffman et al 1977 |
| Api m 6 | — | 71 aa | 7.5 kDa | P83563 | Kettner et al 2001 |

The polypeptide of the invention can also be used for the preparation of a diagnostical composition for diagnosing or identifying subjects allergic to the venom of an insect from the order Hymenoptera. A method of diagnosing an allergy to venom of an insect from the order Hymenoptera is thus provided, comprising the steps of
 a) contacting a subject with a polypeptide of the invention and
 b) detecting an allergic reaction, wherein detecting an allergic reaction indicates said allergy.

In vivo tests for diagnosis of an allergy can easily be adapted to the polypeptide of the invention. Typically, a suitable amount of allergen is injected subcutaneously into a subject's limb, and, after a certain amount of time, the degree of localised inflammation in comparison to controls is determined (skin prick test). Such tests are well known in the art (Hamilton RG, Diagnosis of hymenoptera venom sensitivity, Current Opinion in Allergy Clin Immunol 2(4) (2002) 347-351; Poulsen LK, In vivo and in vitro techniques to determine the biological activity of food allergens, J Chromat B 756 (2001) 41-55; SchmidGrendelmeier P, Crameri R, Recombinant allergens for skin testing, Int Arch Allergy Immunol 125 (2001) 96-111; Williams LW, Bock SA, Skin testing and food challenges in allergy and immunology practice, Clin Rev Allergy Immunol 17(3) (1999) 323-38; Barbee RA, Lebowitz MD, Thompson HC, Burrows B, Immediate skin-test reactivity in a general population sample, Ann Intern Med 84(2) (1976) 129-33).

An allergy to the venom of an insect from the order Hymenoptera can also be diagnosed by an in vitro method comprising the steps of
 a) in vitro contacting a blood sample from a subject with a polypeptide of the invention and
 b) detecting binding of IgE antibodies to the polypeptide, wherein detecting IgE antibodies binding to the polypeptide indicates said allergy.

Binding of IgE antibodies to the polypeptide can, e.g., be detected in an ELISA or by an in vitro release assay employing stripped mast cells and measuring the amount of released mediator, e.g., histamine. To determine specific binding, the results are compared with a specificity control, e.g., with an unrelated antibody. The diagnostic tests can in parallel be carried out to determine the levels of specific IgG (in particular IgG1 and/or IgG4) and/or IgA. For this, an ELISA with specific secondary antibodies recognising the different isotypes can be employed. Parallel testing is particularly useful for following and evaluating a course of specific immunotherapy.

For the therapeutic and diagnostic uses and methods, it is preferred to employ the fusion polypeptides of the invention, nonglycosylated proteins or polypeptides that are capable of binding to IgE from subjects allergic to venom of an insect from the order Hymenoptera, and comprise at least 5, preferably at least 6, 7, 8, 9, 10, 15, 20 or more amino acids of a polypeptide more than 70%, more than 80% or more than 90% homologous or identical to a polypeptide selected from the group consisting of amino acid 26 to 99, 116 to 145, 153 to 158, 185 to 223, 232 to 276 or 362 to 373 of the polypeptide shown in SEQ ID NO: 2. Alternatively, the employed polypeptides are capable of binding to IgE from subjects allergic to venom of an insect from the order Hymenoptera, and comprise at least 5, preferably at least 6, 7, 8, 9, 10, 15, 20 or more amino acids of a polypeptide more than 70%, more than 80% or more than 90% homologous or identical to the polypeptide shown in SEQ ID NO: 2, except for the polypeptides from the group consisiting of amino acids 1 to 34, 63 to 80, 100 to 115, 142 to 149, 168 to 176, 224-239 and 258 to 343 of the polypeptide shown in SEQ ID NO: 2 or except for the polypeptides shown in FIG. 5. Additionally, such polypeptides consisting of amino acids 1 to 25, 146 to 152, 159 to 164, 168 to 184, 224 to 231, and 277 to 361 can be used.

The invention thus also provides a pharmaceutical or diagnostical composition comprising the polypeptide of the invention. Preferentially, the composition further comprises a suitable adjuvant and/or expedient. Optionally, the composition additionally comprises other bee or Hymenoptera venom polypeptides, such as phospholipase A2, hyaluronidase, glucosidase and/or mellitin.

The present invention also relates to a method of diagnosing an allergy to venom of an insect from the order Hymenoptera, comprising the steps of
 a) performing the method of producing a polypeptide encoded by the nucleic acid of the invention, wherein the host cell comprising the expression vector of the invention is cultured under appropriate conditions for expression of said polypeptide, and wherein said polypeptide is purified,
 b) contacting the polypeptide obtained by the method of step a) in vitro with a blood sample,
 c) and detecting binding of IgE antibodies to the polypeptide, wherein detecting IgE antibodies binding to the polypeptide indicates said allergy.

Furthermore, a method of diagnosing an allergy to venom of an insect from the order Hymenoptera is provided, comprising the steps of
 a) performing the method of producing a polypeptide encoded by the nucleic acid of the invention, wherein the host cell comprising the expression vector of the invention is cultured under appropriate conditions for expression of said polypeptide, and wherein said polypeptide is purified,
 b) contacting a subject with the polypeptide obtained by the method of step a) and detecting an allergic reaction, and
 c) detecting an allergic reaction, which is indicative of the allergy.

The invention also provides a method of preparing a composition for diagnosing an allergy to venom of an insect from the order Hymenoptera comprising the step of producing a polypeptide encoded by the nucleic acid of the invention, wherein the host cell comprising the expression vector of the invention is cultured under appropriate conditions for expression of said polypeptide ane said polypeptide is purified and can be used as such for diagnosis. Optionally, the polypeptide is further formulated with stabilizers, such as a neutral protein (e.g., BSA) or detergents to give said composition.

In another embodiment, the invention teaches a method of preparing a composition for treating subjects allergic to the venom of an insect from the order Hymenoptera, comprising the step of performing the method of producing a polypeptide encoded by the nucleic acid of the invention, wherein the host cell comprising the expression vector of the invention is cultured under appropriate conditions for expression of said polypeptide and said polypeptide is purified and can be used as such for therapy. Optionally, the polypeptide is further formulated with appropriate excipient and/or carriers in order to provide said composition. Correspondingly, a method of treating subjects allergic to the venom of an insect from the order Hymenoptera is disclosed, comprising the steps of a) performing the method of producing a polypeptide encoded by the nucleic acid of the invention, wherein the host cell comprising the expression vector of the invention is cultured under appropriate conditions for expression of said polypeptide and said polypeptide is purified, and b) administering the polypeptide obtained by the method of step a) to a subject having such an allergy.

The present invention thus for the first time satisfies the need for a recombinantly produced Hymenoptera venom acid phosphatase or the cDNA encoding this polypeptide, which can be used for diagnostic and therapeutic applications.

EXAMPLES

Example 1

Cloning of CDNA 1.1 Total RNA isolation

Total RNA was isolated from the separated stinger of a honey bee with attached venom sack and additional glands. The isolation of total RNA was performed using a kit according to the manual (peqGold TriFast™, peqlab Biotechnologie GmbH, Erlangen, Germany). The organ was weighed and homogenised in a solution containing guanidiniumisothiocyanate and phenol. Phase separation was induced by addition of chloroform. The aqueous phase was separated after centrifugation, and the containing RNA precipitated with isopropyl alcohol. After washing with diluted ethanol the RNA was dissolved in RNase-free sterile water and used directly in RT-PCR experiments. To prepare RNase-free sterile water cell-culture suitable water was treated with 0.1%. (v/v) diethylpyrocarbonate (DEPC) overnight, and then autoclaved for 20 minutes to destroy DEPC by causing hydrolysis of DEPC.

1.2 cDNA first strand synthesis

Reverse transcriptase was used to synthesise first strand cDNA from the isolated RNA. For this 5 µl of total bee RNA was mixed with 2 µl (20 pmol) oligonucleotide primer and 4 µl DEPC water. An universal oligo-dT of 20 base pair length was used for the purpose of transcribing the poly-adenylated portion of mRNA in the total RNA sample. The reaction mix was incubated at 70° C. for 5 minutes to break secondary structures. After this, the reaction was chilled on ice. Subsequently, 1.5 µl DEPC water, 4 µl 5×reaction buffer, 2 µl dNTP mix (10 mM), and 0.5 µl RNaseOut™ recombinant ribonuclease inhibitor (Invitrogen GmbH, Karlsruhe, Germany) were added. The reaction mix was incubated at 37° C. for 5 minutes. Then 1 µl (200 units) RevertAid™ M-MuLV Reverse Transcriptase (RT, Fermentas GmbH, St. Leon-Rot, Germany) was added and the reaction was incubated at 42° C. for 60 minutes. After this the reaction was stopped by heating to 70° C. for 10 minutes and chilled on ice.

1.3 RT-PCR

First strand cDNA from bee venom gland tissue was used as template for PCR amplification of Api m3 DNA sequences.

Known peptide fragments, public databases and bioinformatics were used to design the specific primers for Api m3. These primers have been designed to allow 5'-end blunt subcloning for native N-terminal expression and 3'-end directed Sac II restriction site subcloning. The nucleotide sequences of the oligonucleotides are:

Api m3 for, 21mer, blunt end: (SEQ ID NO:3)
5'-GAA CTT AAA CAA ATA AAT GTG

Api m3 back 32mer, Sac II site: (SEQ ID NO:4)
5'-AAC CGC GGT TAC TTA CTT ATT CTC AGT ACC CG.

The PCR reaction contained 41 µl DEPC water, 5 µl 10x complete Pfu PCR buffer, 1 µl Api m3 for primer (100 pmol), 1 µl Api m3 back primer (100 pmol), 1 µl dNTP mix (10 mM), 0.5 µl bee venom gland tissue cDNA, and 0.5 µl recombinant Pfu DNA polymerase (Fermentas GmbH, St. Leon-Rot, Germany), to give a total reaction volume of 50 µl. The PCR temperature program for amplification was:

| Step 1: | 96° C., 1 minute |
| Step 2: | 95° C., 30 seconds |
| Step 3: | 55° C., 30 seconds |
| Step 4: | 72° C., 2 minutes |
| Repeat steps 2-4 × 29 times | |
| Step 5: | 72° C., 10 minutes |
| Step 6: | 4° C., until end |

Part of the PCR reaction was run on a 1% agarose (peqGOLD universal agarose, peqlab GmbH, Erlangen, Germany) gel in 0.5x TAE buffer and amplified DNA products visualised with ethidium bromide and UV illumination. A band at the expected size was visible.

1.4 Subcloning for sequencing

DNA from the PCR reaction was isolated using the QIAEX II gel extraction kit (Qiagen GmbH, Hilden, Germany). Subcloning for sequencing was done using the TOPO TA Cloning® Kit (Invitrogen GmbH, Karlsruhe, Germany) with pCR®2.1-TOPO® vector according to the manual. Due to use of Pfu DNA polymerase an initial TA-elongation reaction step with AGS Gold Taq DNA Polymerase (AGS Hybaid, Heidelberg) was introduced. The ligated DNA was transformed into E. coli of the strain TG1 by electroporation (2 mm cuvettes, EasyJect+, Hybaid, Heidelberg, Germany) and selected on ampicillin agar plates.

1.5 Sequencing

The sequencing reaction was done with BigDye® Terminator Cycle Sequencing Kit from ABI (Applied Biosystems Applera Deutschland GmbH, Darmstadt, Germany) according to the manual. 25 cycles were run with a 30 seconds denaturation step at 96° C., 15 seconds annealing step at 50° C., and 4 minutes elongation step at 57° C. Sequencing primer were:

M13/Uni for: (SEQ ID NO:5)
5'-GTA AAA CGA CGG CCA GTG CCA A

M13/Uni rev: (SEQ ID NO:6)
5'-CAG GAA ACA GCT ATG ACC ATG A

The resulting sequence is shown in FIG. 1.

Example 2

Construction Of Expression Vector 2.1 Modification of the insect expression vector For expression of recombinant Api m 3 with potential for native folding and posttranslational modification, the expression in insect cells was chosen. The expression vector pIB/V5-His. (Invitrogen GmbH, Karlsruhe, Germany) was modified to facilitate isolation and purification. A melittin signal sequence for secretion of the recombinant protein was added and the Kozak sequence was optimised for higher expression rates in insect cells. The melittin signal sequence was amplified from total bee RNA, synthesised as described above, using the primers:

```
melt leader for: (SEQ ID NO:7)
5'-GGA AAG CTT TCC GCC ATG GCG AAA TTC TTA GTC melt leader back: (SEQ ID NO:8)
5'-CGG GAT CCC GCA TAG ATG TAA GAA ATG.
```

Underlined are the Hind III and, respectively, BamH I restriction sites in the corresponding primer. The sequence containing the 10x histidine-tag and factor Xa cleavage site has been cloned between the BamH I and EcoR V site of the parent vector. As first template, a tag containing vector was used with the following primers:

```
10 x His for: (SEQ ID NO:9)
5'-CTG AAT AGC GCC GGA TCC GAC CAT 10 x His back: (SEQ ID NO:10)
5'-CCC TCT AGA CTC GAG CCA ATG ATG
```

Underlined are the bases for the introduction of the BamH I restriction site. The resulting fragment was used as second template and further modified to contain a EcoR V site at the 3'-end by use of overlapping primers and PCR extension of the sequence (splice-overlap-extension, SOE). The extension primer used was:

```
SOE Xa: (SEQ ID NO:11)
5'-GGG ATA TCC CTT CCC TCG ATC CCT CTA GAC TC
```

Underlined is the newly introduced EcoR V restriction site for cloning and generation of the expression vector construct. For all PCR steps Pfu DNA polymerase (Fermentas GmbH, St. Leon-Rot, Germany) was used with standard reaction conditions. The annealing temperature was 55° C. for the 10xHistidin fragment amplification and 45° C. for the SOE reaction.

2.2 Re-PCR and subcloning

After sequencing of selected subcloned cDNA clones and verification of the sequence, the clone was used for secondary amplification with Pfu DNA polymerase. The PCR product was subcloned into the EcoR V/Sac II digested expression vector after restriction digest with Sac II.

2.3 Modification of the bacterial expression vector

The verified mammalian expression vector pIB/Mel opt-H10was used as template for the construction of insert for subcloning into the prokaryontic expression vector pET26(+) (Novagen). The PCR program was done according to the temperature gradient given in 1.3. Pfu polymerase was used with the primers:

```
                       (SEQ ID NO: 12)
Api 3 for pro-his    AGAATTTCATATGAAATTCTTAGTCAACG (SEQ ID NO: 13)
Api 3 back pro       AAGAGCTCTTACTTACTTATTCTCAG
```

The amplicon was digested with Sac I and Nde I. The partly digested fragment of correct size was isolated and ligated into the pre-digested vector.

Example 3

Expression of Recombinant Protein 3.1 Transfection

HighFive insect cell (Invitrogen GmbH, Karlsruhe, Germany) were used as hosts for the recombinant expression of Api m 3. DNA was purified from bacterial cultures using the E.Z.N.A. Plasmid Miniprep Kit II (peqlab GmbH, Erlangen, Germany) according to the manual. For transfection of purified DNA into cells the reagent Cellfectin® (Invitrogen GmbH, Karlsruhe, Germany) was used according to the manual.

3.2 Transformation

Vectors have been transformed into prokaryontic cell by electroporation. Cells have been prepared by standard procedures. Electroporation was done with an EasyJecT+instrument (EquiBio, Maidstone, UK) with standard settings according to the manual of the manufacturer.

3.3 Isolation of recombinant protein

The protein was purified according to standard procedures. In brief, prokaryotic cells were disrupted by sonication. Cell membranes etc. were sedimented by ultracentrifugation. The His-tagged protein was then purified from the extract by $Ni^{2+}$ affinity chromatography following the manufacturer's recommendations (e.g., His Trap™ HP Kit, Amersham Biosciences). Purification was controlled by SDS-PAGE. In the case of eukaryotic expression the supernatant medium was collected from confluent stably transfected insect cell expression cultures. The supernatant was adjusted to pH 7.8 and centrifuged at 4000×g for 5 minutes. Aliquots of 10-20 ml medium were applied to a nickel-chelating affinity matrix (NTA-agarose, Qiagen). The column was washed with 10 ml NTA-binding buffer (50 mM sodium phosphate, pH 7.6, 500 mM NaCl) and pre-eluted with NTA-binding buffer containing 20 mM imidazole. The recombinant protein was finally eluted from the matrix with 10 ml NTA-binding buffer containing 400 mM imidazole. Purification was controlled by SDS-PAGE and silver staining of protein.

Example 4

Analysis of recombinant Api m 3

4.1 Sequence alignment and motif analysis

Sequence databases were screened with BLAST algorithms for related sequences of the cloned Api m 3 in other organisms. Sequence alignment was performed with four homologous sequences found in the organisms *Drosophila melanogaster* and *Drosophila subobscura* coding for acid phosphatases. The sequences show significant homologies. The highest homology with 35% is found for Acph-1 from *D. melanogaster*. Amino acids necessary for acid phosphatase activity (RHGXRXP motif (SEQ ID NO: 14)) are highly conserved in the sequence. In addition, four potential N-glycosylation sites (NXS/T motif (SEQ ID NO: 15)) have been identified.

4.2 Tryptic fragment prediction

To verify the cloned sequence matches the expressed recombinant protein a prediction of tryptic fragments was done based on the nucleic acid sequence. The purified protein was digested with sequence grade Trypsin (Sigma-Aldrich Chemie GmbH, Taufkirchen, Germany) according to the instructions of the manufacturer and the resulting peptide fragments were analysed by MALDI-TOF spectrometry using standard protocols. The predicted fragments matched the data acquired by MALDI-TOF and therefore verified the identity of the recombinant protein.

4.3 Enzymatic activity assay

Enzymatic activity of the recombinant enzyme was confirmed according to a described method (Ref. 19).

Example 5

Immunoreactivity of Recombinant Api m 3

Recombinant Api m 3 isolated from stably transfected insect cells was used in an immunoprinting experiment with serum from honey bee venom allergic patients to evaluate IgE reactivity. Diluted honey bee venom and purified recombinant Api m 3 were examined in the same experiment. Proteins were separated on 10% SDS-PAGE gels under reducing conditions. Transfer to nitrocellulose membrane (Protran, Schleicher & Schuell BioScience GmbH, Dassel, Germany) and subsequent immunostaining for sIgE reactive allergens was done using a kit according to the manual (AlaBLOT kit, DPC Biermann GmbH, Bad Nauheim, Germany) showing the immunoreactivity of recombinant Api m 3.

Example 6

Patient Screening With Recombinant Api m 3

Immunoreactivity assays with sera from individual patients To detect specific IgE immunoreactivity of human sera with purified recombinant Api m 3, ELISA plates (NUNC GmbH & Co. KG, Wiesbaden, Germany) were coated with 100 µl of purified recombinant Api m 3 (1 µg/ml) or, as a postive control, purified natural Api m 1 (1 µg/ml) (Latoxan, Valence, France) at 4° C. overnight. For all reaction steps, an ELISA buffer reagent set was used according to the manual (BD Biosciences, Heidelberg, Germany). Appropriate dilutions (1:2; 1:5; 1:10) of the sera were made in assay diluent. Bound IgE was detected with a biotinylated mouse anti-human IgE (BD Biosciences) together with horseradish peroxidase-conjugated avidin, both diluted 1:250 in assay diluent. Color was developed with 100 µl substrate solution per well for 30 minutes in the dark. Finally, 50 µl stop solution were added and plates were read at 450/570 nm. For quality control of the assay, an 8-point human IgE standard curve was run on each plate using murine anti-IgE (10 µg/ml) as capture antibody and human myeloma IgE (Calbiochem-Merck, Darmstadt, Germany) over a concentration range of 31.25 to 4,000 pg/ml (100 µl per well, diluted in assay diluent). Secondary antibody and detection system for total IgE were identical to the one described above for the detection of Api m 1/rApi m 3 sIgE. It could be shown that approximately 37.5% (15/40) of the patient sera that were characterized by a positive sIgE test to honeybee venom had detectable sIgE to recombinant Api m 3. Of 19 patients lacking serologic reactivity to honeybee venom (sIgE <0.35 kU/L), 10 patients were highly sensitized to *Vespula* spp. venom but non-reactive towards honeybee venom (sIgE ≧50 kU/L, FIG. 6B) and 9 were individuals lacking serologic IgE reactivity to both hymenoptera venoms (sIgE <0.35 kU/L to both, vespid and honeybee venom). Only one serum out of the 19 sera lacking serologic reactivity to honeybee venom showed reactivity with recombinant Api m 3. This patient had a clearcut positive sIgE result in the recombinant Api m 3 ELISA. He reported to the allergy service with a history of a severe anaphylactic reaction after a hymenoptera sting. The offending insect was not identified by the patient. Despite a negative "classical" serologic result and a negative intradermal skin test, the patient was finally classified as an honey bee venom allergic patient. It can be assumed that he reacts strongly to native Api m 3 with is likely to be underrepresented in clinical test kits and therefore his allergy was not noticed.

FIGURE LEGENDS

FIG. 1 shows the nucleotide sequence of the isolated cDNA for Api m 3 (SEQ ID NO: 1).

FIG. 2 shows the predicted restriction enzyme pattern of the isolated cDNA for Api m 3.

FIG. 3 shows the predicted translated amino acid sequence of the isolated cDNA for Api m 3 (SEQ ID NO:2). The underlined peptides can be aligned to prior published fragments. See FIGS. 5 and 6.

FIG. 4A shows a vector map of a preferred insect cell expression vector, pIB/Mel opt-H10 api m 3. The vector was modified to include a N-terminal loxhistidine-tag, cleavable with factor Xa protease as well as the signal sequence of bee melittin for secreted expression. The gene of interest was cloned between the EcoR V and Sac II site. The gene comprises a stop codon at the 3'-end. The expressed protein should be secreted and will have a factor Xa cleavable 10x histidine-tag at the N-terminus.

FIG. 4B shows optimisation of the Kozak sequence for insect cell expression. The former sequence a) (SEQ ID NO: 17) was changed into b) (SEQ ID NOS: 18 and 19, respectively, in order of appearance) to be in accordance with the preferred translation initial sequence (G/A)NNATGG (SEQ ID NO: 16) adding an alanine to the N-terminal sequence.

Figure 4C:
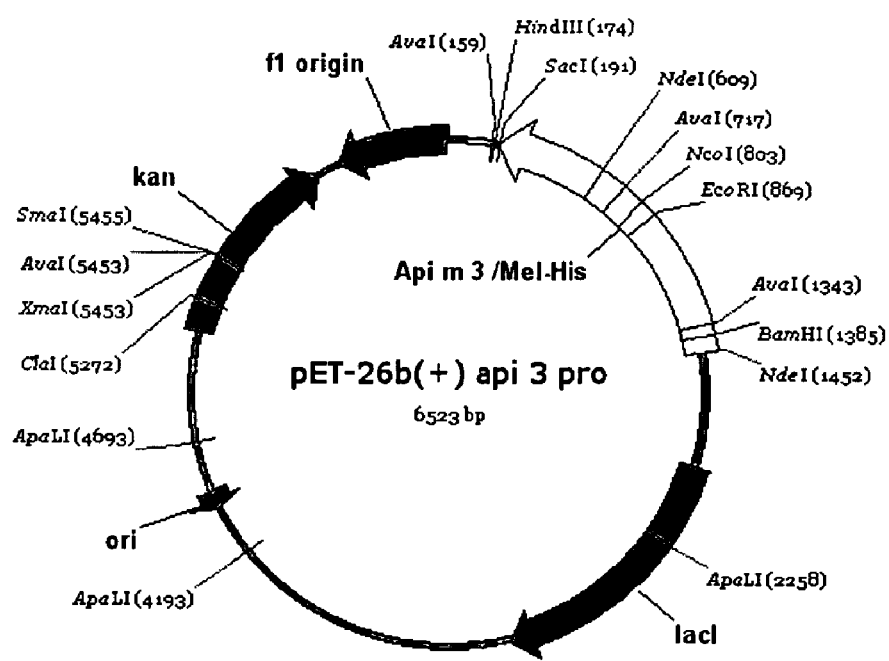

FIG. 4C shows a vector map of a preferred bacterial expression vector, pET26(+) api 3 pro. The vector was modified to contain the gene of interest between the Sac I and Nde I site. The protein sequence was taken from the verified mammalian expression vector pIB/Mel opt-H10 api m 3.

FIG. 5A shows the sequence information of potential peptide fragments of acid phosphatase publicly known prior to this invention. Peptide fragments (SEQ ID NOS 20-26, respectively, in order of appearance) are listed in order of alignment to human and rat prostate phosphatase as published in Ref 20. The alignment order of fragments to derived sequence is given in the second column. Positions of aligned peptide segments can be taken from FIG. 3 and F*ig*. 5B, as well as FIG. 6. Highlighted sequence segments in the third column show amino acids present in the Api m 3 sequence. The fourth column shows the length of the published peptide fragments.

FIG. 5B shows the corrected alignment of peptides originally postulated by Hoffmann et al. (Ref. 20) to Api m 3 (SEQ ID NO: 2). "Hoffman" sequences are disclosed as SEQ ID NOs 20-26, respectively, in order of appearance. "Revised" sequences are disclosed as SEQ ID NOs 27, 22 and 28-32, respectively, in order of appearance.

Figure 6:
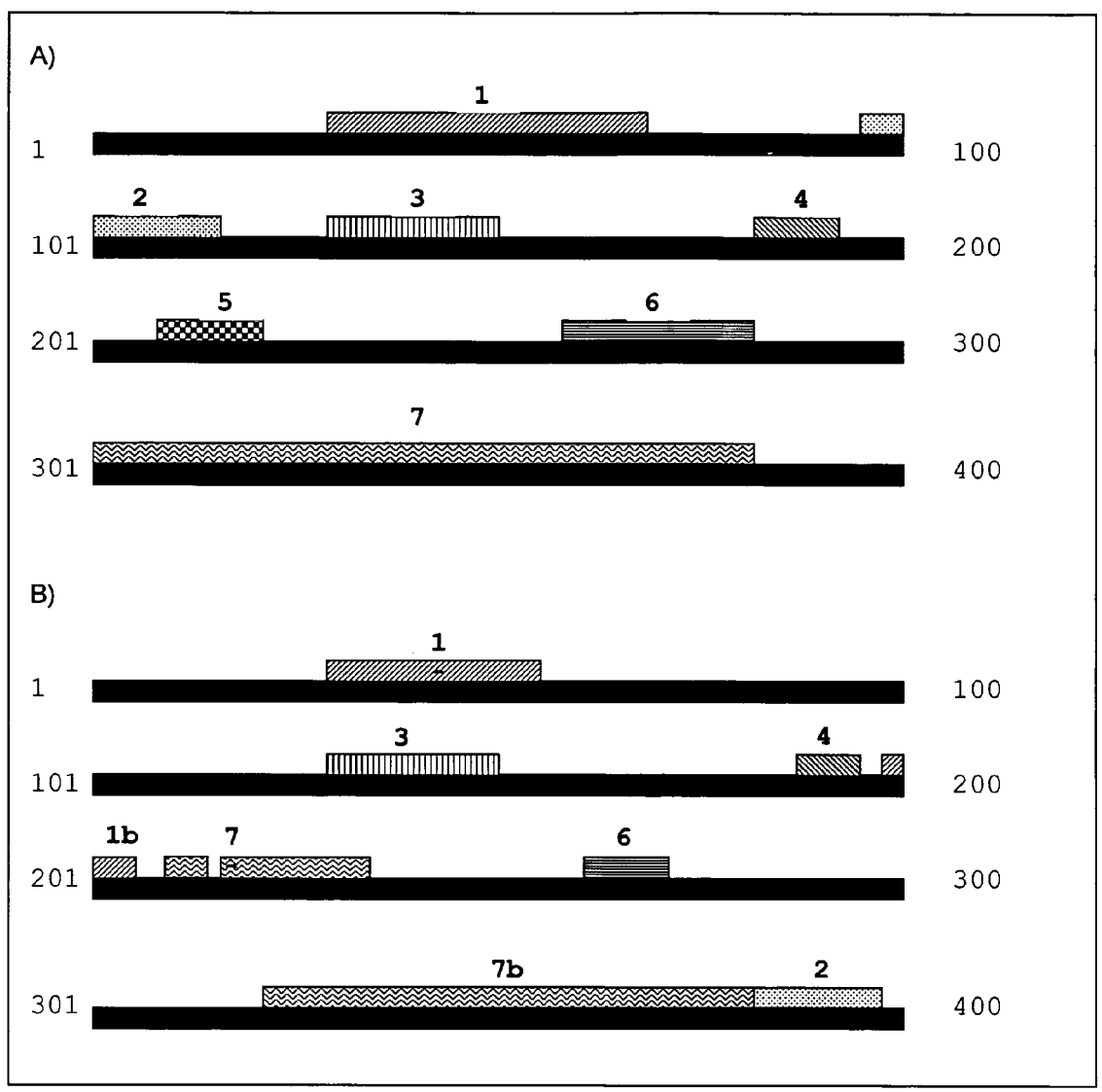

FIG. 6 shows a schematic alignment of peptides postulated by Hoffman et al. (Ref. 20) (A), in comparison to the corrected oder after cloning and sequencing of the Api m 3 gene (B). It is obvious that the alignment differs from the published alignment with human and rat prostate phosphatase (Ref. 20). The published peptide fragments can not be aligned to match the sequence as would be expected. Firstly, the order of alignment positions is different from the publication. Secondly, some fragments, like fragments 1 and 7 partially align at different sites in the sequence, and therefore are not continuous peptides derived from a cDNA sequence. Furthermore, some published fragment sequences, like fragment 5, cannot be aligned at all. The scheme also shows the leader peptide and is not exact regarding the number of amino acids.

FIG. 7 depicts recombinant Api m 3 expression and purification. Shown is a 10% silver stained SDS-PAGE gel. Lane 1, protein molecular weight standards; lane 2, diluted bee venom; lane 3, purified recombinant Api m 3 derived from insect cell expression; lane 4, supernatant from cells stably transfected with recombinant Api m 3.

FIG. 8 Alignment of Api m 3 to acid phosphatase sequences. Shown is the alignment of cloned Api m 3 to different insect acid phosphatases with significant homology. The highest homology with 35% is found for Acph-1 from *D. melanogaster*. Amino acids necessary for acid phosphatase activity and for glycosylation are shaded in grey. FIG. 8 shows SEQ ID NOS: 14, 2 and 33-36, respectively in order of appearance.

FIG. 9 Results from MALDI-TOF spectrometry in comparison with predicted tryptic fragments. Experimental data are in accordance with the prediction. FIG. 9 discloses SEQ ID NOS: 37-39, 31 and 40-41, respectively, in order of appearance.

FIG. 10 shows the enzymatic activity of purified recombinant Api m 3. Shown is the acid phosphatase enzymatic activity of recombinant Api m 3 dependent on the amount of protein used. The experiment was performed according to Ref 19.

FIG. 11 shows an IgE immunoblot of pooled honey bee venom-reactive patient serum with recombinant Api m 3. Lane 1, protein molecular weight standards; lane 2, diluted bee venom; lane 3, purified recombinant Api m 3 derived from insect cell expression.

FIG. 12A Immunoreactivity of 59 individual patient sera with recombinant Api m 3. Shown are the results of an ELISA assay measuring the IgE antibody reactivity with Api m 3. A, 40 honey bee venom-sensitized patients (1-40; sIgE to honey bee venom ≧0.35 kU/L).

FIG. 12B 19 honey bee venom-negative patients (41-50; sIgE to honey bee venom <0.35 kU/L and to vespid venom ≧ 50 kU/L) (51-59; sIgE to honey bee and vespid venom <0.35 kU/L).

FIG. 12C 8-point calibration ELISA standard for total human IgE (31.25; 62.5; 125; 250; 500; 1,000; 2,000; 4,000 pg/ml).

REFERENCES

1. Helbling A et al., Incidence of anaphylaxis with circulatory symptoms: a study over a 3-year period comprising 940,000 inhabitants of the Swiss Canton Bern, Clin Exp Allergy 34, 285-290 (2004).
2. Eich-Wanger C, Muller UR, Bee sting allergy in beekeepers. Clin Exp Allergy 28, 1292-98 (1998).
3. Dotimas EM, Hider RC, Honeybee venom, Bee World 68(2) 51-70 (1987).
4. Skenderov, Ivanov, Bienenprodukte, Zemizdat Verlag Sofia (Bulgaria),(1983).
5. Habermann, E, Bienen- und Wespenstiche aus medizinischer Sicht, Allgemeine Deutsche Imkerzeitung (ADIZ) 11 p., 301-304 (1974).
6. Kulike, H, Zur Struktur und Funktionsweise des Hymenopterenstachels, Amts- und Mitteilungsblatt der Bundesanstalt fur Materialprufung 16 p., 519-550 (1986).
7. Sobotka A, Franklin R, Valentine M, Adkinson NF, Lichtenstein LM, Honey bee venom: Phospholipase A as the major allergen, J Clin Allergy Clin Immunol 53,103 (1974).
8. Sobotka AK, Franklin RM, Adkinson NF, Valentine MD, Baer H, Lichtenstein LM. Allergy to insect stings. II. Phospholipase A: The major allergen in honeybee venom, J Allergy Clin Immunol 57, 29-40 (1976).
9. Hoffman DR, Shipman WH, Allergens in bee venom. I. Separation and identification of the major allergen, J Allergy Clin Immunol 58, 551-62 (1976).
10. Kuchler K, Gmachl M, Sippl MJ, Kreil G, Analysis of the cDNA for phospholipase A2 from honeybee venom glands. The deduced amino acid sequence reveals homology to the corresponding vertebrate enzymes, Eur. J. Biochem. 184, 249-254 (1989).
11. Gmachl M, Kreil G, Bee venom hyaluronidase is homologous to a membrane protein of mammalian sperm; Proc. Natl. Acad. Sci. U.S.A. 90, 3569-3573 (1993).
12. Vlasak R, Unger-Ullmann C, Kreil G, Frischauf A-M, Nucleotide sequence of cloned cDNA coding for honeybee prepromelittin, Eur. J. Biochem 135, 123-126 (1983).
13. Hoffman DR, Shipman WH, Babin D, Allergens in bee venom II. Two new high molecular weight allergenic specificities, J Allergy Clin Immunol. 59(2), 147-53 (1977).
14. Kettner A, Hughes GJ, Frutiger S, Astori M, Roggero M, Spertini F, Corradin G, Api m 6: a new bee venom allergen, J. Allergy Clin. Immunol. 107, 914-920 (2001).
15. Kettner A, Henry H, Hyghes G, Corradin G, Spertini F, IgE and T-cell responses to high-molecular weight allergens from bee venom, Clin Exp Allergy 29, 394-401 (1999).
16. King TP, Spangfort MD, Structure and Biology of Stinging Insect Venom Allergens, Int Arch Allergy Immunol 123, 99-106 (2000).
17. Arbesman CE, Reisman RE, Wypych JI. Allergenic potency of bee antigens measured by RAST inhibition, Clinical Allergy 6, 587-94 (1976).
18. Soldatova LN, Bakst JB, Hoffman DR, Slater JE, Molecular cloning of a new honey bee allergen, acid phosphatase, J. Allergy Clin. Immunol. 105, S378 (2000).
19. Barboni E, Kemeny DM, Campos S, Vernon CA, The purification of acid phosphatase from honey bee venom (Apis mellifica), Toxicon 25(10), 1097-103 (1987).
20. Hoffman DR, Hymenoptera venom proteins, in Natural Toxins 2, Edts. Singh BR and Tu AT, Plenum Press, New York 169-186 (1996).
21. King TP, Molecular approaches to the study of allergens, Allergy 28, 84-100. (1990).
22. MUller UR, Recombinant Hymenoptera venom allergens, Allergy 57, 570-576 (2002).
23. MUller UR, New Developments in the Diagnosis and Treatment of Hymenoptera Venom Allergy, Int. Arch Allergy Immunol, 124, 447-453 (2001).
24. Wypych JI, Abeyounis CJ, Reisman RE, Analysis of differing patterns of cross-reactivity of Honeybee and Yellow jacket venom-specific-IgE: Use of purified venom fractions. Int Arch Allergy Appl Immunol 89, 60-6 (1989).

25. Castro FFM, Palma MS, Brochetto-Braga MR, Malaspina O, Lazaretti J, Baldo MAB, Biochemical properties and study of antigenic cross-reactivity between Africanized honey bee and wasp venom, J Invest Allergol Clin Immunol 4, 37-41 (1994).
26. Hoffman DR, Dove, De, Moffitt JE, Stafford CT. Allergens in Hymenoptera venom XII. Cross-reativity and multiple reactivity between fire ant venom, bee and wasp venoms, J Allergy Clin Immunol 82, 828-34 (1988).
27. Jacobsen RS, Hoffmann DR. Honey-bee acid phosphatase is a member of the prostatic acid phosphatase family. J Allergy Clin Immunol 95, 372 (1995).
28. Sudowe S, Montermann E, Steitz J, Tuting T, Knop J, Reske-Kunz AB. Efficacy of recombinant adenovirus as vector for allergen gene therapy in a mouse model of type I allergy. Gene Ther 9, 147-56 (2002).
29. Hunt KJ, Valentine MD, Sobotka AK, Benton AW, Lichtenstein LM. A controlled study of immunotherapy in insect hypersensitivity. New Engl. J. Med. 229, 157 (1978).
30. Schiavino D, Nucera E, Pollastrini E, De Pasquale T, Buonomo A, Bartolozzi F, Lombardo C, Roncallo C, Patriarca G. Specific ultrarush desensitization in Hymenoptera venom-allergic patients. Ann Allergy Asthma Immunol, 92(4):409-13 (2004).

The invention claimed is:

1. An isolated nucleic acid molecule comprising a nucleic acid sequence encoding the polypeptide with the amino acid sequence set forth in SEQ ID NO: 2.

2. The isolated nucleic acid molecule of claim 1, wherein said polypeptide is encoded by the nucleotide sequence of SEQ ID NO: 1.

3. An isolated nucleic acid molecule encoding the polypeptide of SEQ ID NO: 2 with a mutated putative glycosylation site, wherein the putative glycosylation site has the amino acid sequence of Asn-Xaa-Ser or Asn-Xaa-Thr.

4. An isolated nucleic acid molecule consisting of at least 21 contiguous nucleotides of nucleotides 78 to 299, 348 to 437, 459 to 476, 555 to 671, 696 to 830 or 1086 to 1121 of the nucleic acid sequence of SEQ ID NO: 1.

5. The isolated nucleic acid molecule of claim 1, wherein said isolated nucleic acid molecule is from an insect that is a bee from the genus *Apis*.

6. The isolated nucleic acid molecule of claim 5, wherein the bee is *Apis mellifera*.

7. An expression vector comprising a nucleic acid sequence encoding a polypeptide comprising the sequence set forth in SEQ ID NO: 2 operationally linked to an expression control sequence.

8. The expression vector of claim 7, wherein the nucleic acid sequence is linked in frame to a second nucleic acid sequence encoding an additional polypeptide.

9. The expression vector of claim 8, wherein the additional polypeptide is selected from the group consisting of a poly-Histidine tag, glutathione -S-transferase, β-galactosidase, a cytokine, an IgG-Fc, and another Hymenoptera venom protein or antigenic fragment thereof.

10. The expression vector of claim 7, wherein the vector is suitable for expression in bacterial or insect cells.

11. The expression vector of claim 7, wherein the vector is pIB/Mel opt-H10-Api m3 or pET26(+) api 3 pro.

12. An isolated host cell comprising an expression vector comprising a nucleic acid sequence encoding a polypeptide comprising the sequence set forth in SEQ ID NO: 2 operationally linked to an expression control sequence.

13. The isolated host cell of claim 12, wherein the cell is an insect cell or a bacterial cell.

14. A method of producing a polypeptide comprising culturing a host cell comprising an expression vector comprising a nucleic acid sequence encoding a polypeptide comprising the sequence set forth in SEQ ID NO: 2 linked to an expression control sequence under appropriate conditions for expression of said polypeptide and purifying said polypeptide.

15. A method of preparing a composition for diagnosing an allergy to venom of an insect from the order Hymenoptera comprising producing a polypeptide by culturing a host cell comprising an expression vector comprising a nucleic acid sequence encoding a polypeptide comprising the sequence set forth in SEQ ID NO: 2 operationally linked to an expression control sequence under appropriate conditions for expression of said polypeptide and purifying said polypeptide.

16. A method of preparing a composition, comprising producing a polypeptide by culturing a host cell comprising an expression vector comprising a nucleic acid sequence encoding a polypeptide comprising the sequence set forth in SEQ ID NO: 2 operationally linked to an expression control sequence under appropriate conditions for expression of said polypeptide and purifying said polypeptide.

17. The isolated nucleic acid molecule of claim 1, wherein said polypeptide is acid phosphatase (Api m 3) from a species of the order Hymenoptera.

18. The expression vector of claim 7, wherein said nucleic acid sequence is set forth in SEQ ID NO: 1.

19. The isolated host cell of claim 12, wherein said nucleic acid sequence is set forth in SEQ ID NO: 1.

20. The method of claim 14, wherein said nucleic acid sequence is set forth in SEQ ID NO: 1.

21. The method of claim 15, wherein said nucleic acid sequence is set forth in SEQ ID NO: 1.

22. The method of claim 16, wherein said nucleic acid sequence is set forth in SEQ ID NO: 1.

23. An isolated nucleic acid molecule consisting of at least 21 contiguous nucleotides of the nucleic acid sequence of SEQ ID NO: 1, wherein said contiguous nucleotides encode a polypeptide selected from the group consisting of amino acids 26 to 99, 116 to 145, 153 to 158, 232 to 276 and 362 to 373 of the polypeptide shown in SEQ ID NO: 2.

* * * * *